United States Patent
Suzuki et al.

(10) Patent No.: US 8,506,298 B2
(45) Date of Patent: Aug. 13, 2013

(54) DENTAL FILLING/RESTORATION KIT

(75) Inventors: Takeshi Suzuki, Tokyo (JP); Hideki Kazama, Tokyo (JP)

(73) Assignee: Tokuyama Dental Corporation (JP)

( * ) Notice: Subject to any disclaimer, the term of this patent is extended or adjusted under 35 U.S.C. 154(b) by 0 days.

(21) Appl. No.: 12/602,921

(22) PCT Filed: Jun. 5, 2008

(86) PCT No.: PCT/JP2008/060363
§ 371 (c)(1),
(2), (4) Date: Dec. 3, 2009

(87) PCT Pub. No.: WO2008/149929
PCT Pub. Date: Dec. 11, 2008

(65) Prior Publication Data
US 2010/0216096 A1    Aug. 26, 2010

(30) Foreign Application Priority Data

Jun. 7, 2007 (JP) ................................. 2007-152064
Mar. 19, 2008 (JP) ................................. 2008-070927

(51) Int. Cl.
*A61C 5/04* (2006.01)
*A61C 5/00* (2006.01)

(52) U.S. Cl.
USPC ......... 433/217.1; 523/118; 523/120; 523/116

(58) Field of Classification Search
USPC ....... 523/118, 116, 120; 522/184; 433/217.1
See application file for complete search history.

(56) References Cited

U.S. PATENT DOCUMENTS

| | | | |
|---|---|---|---|
| 5,849,813 A * | 12/1998 | Oxman | 523/116 |
| 5,922,786 A * | 7/1999 | Mitra et al. | 523/118 |
| 5,925,690 A * | 7/1999 | Fuchigami et al. | 523/118 |
| 6,174,935 B1 * | 1/2001 | Matsunae et al. | 523/118 |
| 6,288,138 B1 * | 9/2001 | Yamamoto et al. | 523/118 |
| 6,291,548 B1 * | 9/2001 | Akahane et al. | 523/116 |
| 6,682,881 B2 | 1/2004 | Haijima | |
| 6,759,449 B2 * | 7/2004 | Kimura et al. | 523/118 |
| 6,849,670 B2 * | 2/2005 | Satoh et al. | 522/64 |
| 2003/0162863 A1 * | 8/2003 | Satoh et al. | 523/109 |
| 2004/0077746 A1 * | 4/2004 | Takeshita et al. | 523/116 |
| 2005/0009946 A1 * | 1/2005 | Oguri et al. | 522/184 |
| 2006/0247328 A1 * | 11/2006 | Nakata et al. | 523/109 |
| 2008/0081889 A1 | 4/2008 | Kawashima et al. | |

FOREIGN PATENT DOCUMENTS

| | | |
|---|---|---|
| EP | 1454921 A1 | 9/2004 |
| JP | 2001-72523 A | 3/2001 |
| JP | 2003-81731 A | 3/2003 |
| JP | 2003-96122 A | 4/2003 |
| JP | 2004-43427 A | 2/2004 |
| JP | 2006-131612 A | 5/2006 |
| JP | 2007-210944 A | 8/2007 |
| WO | 2006/016545 A1 | 2/2006 |

OTHER PUBLICATIONS

Worksheet titled: Weight calculations 12602921.*
International Search Report for International Application No. PCT/JP2008/060363 mailed Sep. 9, 2008 with English Translation.
Notice of Reasons for Rejection for Japanese Application No. 2008-146901, mailed Feb. 5, 2013, with English translation.
Database WPI Week 200638 Thomson Scientific, London, GB; AN 2006-36778. XP002696007 & JP 2006 131621 A (San Medical KK); May 25, 2006—Abstract.
Extended European Search Report issued in European Application No. 08765176.6 dated May 13, 2013; 7 pages.

* cited by examiner

Primary Examiner — James J Seidleck
Assistant Examiner — Peter A Salamon
(74) Attorney, Agent, or Firm — Cantor Colburn LLP

(57) ABSTRACT

Provided is a dental filling/restoration kit, in which a pretreatment material and a filling/restoring material can be cured by only one irradiation with light, which enables further improved adhesion between a tooth and the filling/restoring material, which prevents the filling/restoring material from being easily colored, to thereby exhibit its excellent sensuousness. Specifically provided is a dental filling/restoration kit which includes: a filling/restoring material (A) containing 100 parts by mass of a radical-polymerizable monomer (a) containing 3 to 30 parts by mass of a water-soluble radical-polymerizable monomer having no acidic group (a1), a photopolymerization initiator (b), and a filler (c), the filler (c) being contained in an amount of 80 to 2,000 parts by mass relative to 100 parts by mass of the radical-polymerizable monomer (a); and a pretreatment material (B) containing a radical-polymerizable monomer having an acidic group (d) and water (e).

6 Claims, No Drawings

DENTAL FILLING/RESTORATION KIT

CROSS REFERENCE TO RELATED APPLICATIONS

This is a U.S. national stage of application No. PCT/JP2008/060363, filed on 5 Jun. 2008. Priority under 35 U.S.C. §119(a) and 35 U.S.C. §365(b) is claimed from Japanese Application No. 2007-152064, filed 7 Jun. 2007 and Japanese Application No. 2008-070927, filed 19 Mar. 2008, the disclosure of which is also incorporated herein by reference.

TECHNICAL FIELD

The present invention relates to a dental filling/restoration kit containing a photopolymerizable dental restoring material.

BACKGROUND ART

Conventionally, a small loss (cavity) formed due to the decay or the like of a tooth has been filled with a metal material. However, recently, because the color tone comparable to a natural tooth color can be provided and an operation is easy, a filling/restoring material containing an acrylic polymerizable monomer, an inorganic filler, and a photopolymerization initiator has been used preferably.

However, the above-mentioned resin-based filling/restoring material has no adhesiveness with respect to a tooth. Therefore, when a cavity of a tooth is filled with only a resin-based filling/restoring material, a gap may be formed between the filling/restoring material and the tooth. This increases a risk that a bacterium enters through the gap or the filling/restoring material comes off the tooth.

Then, the idea of providing a layer of a pretreatment material containing, as a main component, a monomer or the like having an acidic group between the resin-based filling/restoring material and the tooth has been realized. The pretreatment material functions as a surface treatment agent for an enamel and a dentin of a tooth and enhances the adhesion between the filling/restoring material and the tooth. The filling/restoring material and the tooth can be attached to each other without any gap by interposing such a pretreatment material between the tooth and the resin-based filling/restoring material.

It is preferred that the filling/restoring material can be deformed easily when provided with the shape of a tooth and be cured immediately after the completion of filling. Therefore, the filling-restoring material and the pretreatment material contain a photopolymerization initiator, and are cured preferably using visible light that is harmless to a living body.

The operation of restoring a tooth is performed in the following procedure. First, a decayed tooth portion is drilled to form a cavity. Then, the cavity is coated with a pretreatment material. Then, in order to cure the pretreatment material, the portion coated with the pretreatment material is irradiated with visible light. Then, on the layer of the pretreatment material a filling/restoring material is filled. Finally, in order to cure the filling/restoring material, the filling/restoring material is irradiated with visible light.

In the case of the above-mentioned restoration method, it is necessary to irradiate the filling/restoring material with visible light twice. However, it is desired to reduce the number of irradiation with visible light in terms of the alleviation of a burden on a patient and the simplification of a restoration operation.

However, when the pretreatment material and the filling/restoring material are cured concurrently by one irradiation with visible light, a large stress is generated at an adhesion interface due to a large polymerization contraction amount of the filling/restoring material. As a result, there may easily arise a problem that the adhesive strength between the pretreatment material and the filling/restoring material becomes very small or adhesion durability during a long period of time becomes poor.

In order to solve the above-mentioned problem, a dental filling kit has been proposed, which contains a monomer having an acidic group, a monomer having no acidic group, and a polymerization initiator in both the filling/restoring material and the pretreatment material (see, for example, Patent Document 1). In the kit, the filling/restoring material is formed of a composition similar to that of the pretreatment, and hence, the affinity of the interface between the pretreatment material and the filling/restoring material is enhanced, which makes it difficult for the pretreatment material and the filling/restoring material to peel off at the interface. Thus, even in the case where the pretreatment and the filling/restoring material are polymerized concurrently by only one irradiation with light, relatively high adhesive strength is obtained.

Patent Document 1: JP 2006-131612 A (claim 1 or the like)

DISCLOSURE OF THE INVENTION

Problem to be Solved by the Invention

However, the prior art disclosed in the above-mentioned Patent Document 1 has the following problem. This is the problem that the adhesion and adhesion durability of a tooth and a filling/restoring material are poor compared with those in the case of two irradiations with visible light. That is, there is a problem that a filling/restoring material that fills a cavity is likely to come off.

The filling/restoring material used in the above-mentioned prior art contains a monomer having an acidic group, and hence, the filling/restoring material is likely to adsorb a basic substance contained in food and the like. Therefore, a portion of the filling/restoring material is colored, which causes a problem of lacking of sensuousness.

An object of the present invention is thus to provide a dental filling/restoration kit in which a pretreatment material and a filling/restoring material can be cured by only one irradiation with light, and which can enhance the adhesion between the tooth and the filling/restoring material and is unlikely to be colored to exhibit excellent sensuousness.

Means for Solving the Problems

In order to achieve such an object, the inventor has studied earnestly, and consequently, found the following: a cavity is pretreated with a pretreatment material containing a radical-polymerizable monomer having an acidic group and water; thereafter, the cavity is filled with a filling/restoring material containing a water-soluble radical-polymerizable monomer having no acidic group; the filling/restoring material is cured by irradiation with visible light; and, as a result, even when the pretreatment material and the filling/restoring material are polymerized by only one irradiation with light, the stable and high adhesion is expressed between the tooth and the filling/restoring material and the filling/restoring material is unlikely to be colored, thereby achieving the present invention.

In particular, the present invention relates to a dental filling/restoration kit including: a filling/restoring material (A)

containing 100 parts by mass of a radical-polymerizable monomer having no acidic group (a) containing 3 to 30 parts by mass of a water-soluble radical-polymerizable monomer having no acidic group (a1), a photopolymerization initiator (b), and 80 to 2,000 parts by mass of a filler (c); and a pretreatment material (B) containing a radical-polymerizable monomer having an acidic group (f) and water (g), in which the filling/restoring material (A) is directly filled in a cavity coated with the pretreatment material (B), which is uncured.

Further, another aspect of the present invention relates to a dental filling/restoration kit, in which the photopolymerization initiator (b) includes an acylphosphine oxide-based polymerization initiator.

When a dental filling/restoration kit using a photopolymerization initiator with such a composition is adopted, the adhesion between the tooth and the filling/restoring material can be increased further. Thus, the filling/restoring material can be effectively prevented from peeling off from the tooth.

Further, still another aspect of the present invention relates to a dental filling/restoration kit, in which the filling/restoring material (A) further includes a tertiary amine compound (d) and a basic inorganic material (e).

According to the present invention, on the pretreatment material applied to a tooth the filling/restoring material containing a tertiary amine compound and a basic inorganic material is filled, whereby a neutralization reaction is effected between the basic inorganic material with a relatively high basicity and the acidic group of the radical-polymerizable monomer having an acidic group in the pretreatment material at the contact interface between the pretreatment material and the filling/restoring material, an acid of the acidic group is weakened, and the decrease of the effect of promoting the polymerization of the tertiary amine compound can be avoided. Consequently, the tertiary amine compound can exhibit the effect of promoting the polymerization sufficiently at the contact interface between the pretreatment and the filling/restoring material.

Further, the radical-polymerizable monomer contained in the filling/restoring material does not contain an acidic group, and the radical-polymerizable monomer contained in the pretreatment material contains an acidic group. Thus, the pH of the former monomer is higher than that of the latter monomer, and hence, a pH gradient is formed between the filling/restoring material and the pretreatment material. As a result, the filling/restoring material and the pretreatment material are fused to form a mixed layer. Further, a neutralization reaction is effected between the basic inorganic material and the acidic group. Therefore, even in this mixed layer, the effect of promoting photopolymerization due to the presence of the tertiary amine compound is unlikely to be lost.

Thus, even in the case where the thickness of the filling/restoring material is large, and the light reaching the pretreatment material side by irradiation with light during curing is weak, the polymerization on the pretreatment material side can be effected sufficiently. As a result, high adhesive strength can be realized between the tooth and the filling/restoring material. Further, because the filling/restoring material does not contain a radical-polymerizable monomer containing an acidic group, the filling/restoring material is unlikely to be colored. Therefore, a dental filling/restoration kit capable of realizing a filling excellent in sensuousness is obtained.

Further, still another aspect of the present invention relates to a dental filling/restoration kit, in which the filling/restoring material (A) includes at least 3 parts by mass of the basic inorganic material (e) based on 100 parts by mass of the radical-polymerizable monomer having no acidic group (a).

When the filling/restoring material with such a composition is used, the sufficient effect of promoting polymerization during polymerization is obtained. Therefore, further stable and high adhesion is expressed between the tooth and the filling/restoring material.

Further, still another aspect of the present invention relates to a dental filling/restoration kit, in which the tertiary amine compound (d) is an aromatic amine compound.

By using the aromatic tertiary amine compound with a relatively low basicity, the aromatic tertiary amine compound is unlikely to effect a neutralization reaction with an acidic group of the radical-polymerizable monomer containing an acidic group in the pretreatment material. This further enhances the high effect of promoting the polymerization of a photopolymerization initiator at the contact interface between the pretreatment material and the filling/restoring material and the inside of the pretreatment material and the filling/restoring material, which can largely contribute to the promotion of the photopolymerization.

Further, still another aspect of the present invention relates to a dental filling/restoration kit, in which the basic inorganic material (e) is fluoroaluminosilicate glass.

When the dental filling/restoration kit with such a composition is adopted, polyvalent metal ions eluted from fluoroaluminosilicate glass are subjected to ion cross-linking with a polymerized substance of the radical-polymerizable monomer having an acidic group, whereby the adhesiveness with respect to a dentin and the physical properties of a cured substance can be enhanced.

Further, still another aspect of the present invention relates to a dental filling/restoration kit, in which the pretreatment material (B) and the filling/restoring material (A) further include a vanadium compound and hydroperoxide, respectively.

When the dental filling/restoration kit with such a composition is adopted, the adhesion between the tooth and the filling/restoring material can be enhanced further.

Effect of the Invention

The present invention contributes to curing a pretreatment material and a filling/restoring material by only one irradiation with light, further enhancing the adhesion between a tooth and the filling/restoring material, and preventing the filling/restoring material from being easily colored, to thereby exhibit its excellent sensuousness.

BEST MODE FOR CARRYING OUT THE INVENTION

Hereinafter, preferred embodiments of the dental filling/restoration kit according to the present invention is described. It should be noted that the present invention is not limited to the embodiments described below.

The dental filling/restoration kit according to an embodiment of the present invention roughly contains a filling/restoring material (hereinafter, referred to as a composite resin) and a pretreatment material (hereinafter, referred to as a primer). The composite resin contains a water-soluble radical-polymerizable monomer having no acidic group, and the primer contains a radical-polymerizable monomer having an acidic group. Part of the radical-polymerizable monomer having no acidic group contained in the composite resin is soluble in water, and hence, the composite resin has high affinity with the acidic group of the radical-polymerizable monomer contained in the primer. Therefore, the affinity between the composite resin and the primer is high. Further, the composite resin contains a radical-polymerizable monomer having no acidic group and the primer contains a radical-polymerizable monomer having an acidic group; therefore, the pH of the composite resin is higher than that of the primer. Thus, a pH gradient is formed between the composite resin and the primer. As a result, the radical-polymerizable monomer moves to both the composite resin and the primer at the interface therebetween, and both the layers are fused. Further, when the radical-polymerizable monomer having no acidic group contained in the composite resin proceeds to the primer side, the photopolymerization initiator also migrates from the composite resin side to the primer side. Therefore, even if the photopolymerization initiator is not added to the primer, the primer can be polymerized.

On the other hand, an amine compound is generally added to the filling/restoring material as a polymerization initiator. By using the amine compound in combination with the photopolymerization initiator, the curing speed is enhanced and larger curing depth can be ensured, and even the filling/restoring material at a site far away from the light-irradiation surface of the filling/restoring material filling a tooth, i.e., at a site closer to a tooth surface can be cured with light sufficiently. As such an amine compound, an aromatic tertiary amine compound is widely used considering particularly high activity. However, the tertiary amine compound exhibits a weak basicity. Therefore, when the composite resin contains an acidic group, the neutralization reaction is effected between the tertiary amine compound and the acidic group. Then, consequently, the effect of promoting the polymerization of the aromatic tertiary amine in the composite resin decreases immediately after the production of the composite resin.

Further, a dental filling/restoration kit is known, in which the photopolymerization of a pretreatment material is effected earlier by adjusting the amount of a polymerization inhibiting agent or a photopolymerization initiator contained in a composite resin and a primer (see, for example, JP 2007-210944 A (claims)). In the case where a primer applied to a tooth surface and a composite resin filling the primer layer is cured by irradiation with light concurrently in such a dental filing/restoration kit, the photopolymerization of the primer layer is effected earlier, and hence, similarly, peeling becomes unlikely to occur at the interface between the primer layer and the composite resin. Thus, even in the case where the primer and the composite resin are polymerized concurrently by only one irradiation with light, relatively high adhesive strength is obtained.

However, even in the dental filling/restoration kit described in JP 2007-210944 A, when the thickness of the filling/restoring material becomes large, the polymerization on the pretreatment material side where light is unlikely to reach tends to be delayed. Further, in the vicinity of the interface at which the pretreatment material and the filling/restoring material are in contact with each other, similarly, the amine compound in the filling/restoring material is neutralized by a monomer having an acidic group in the pretreatment material, and the effect of promoting the polymerization decreases. Therefore, there is a problem that the polymerization of the filling/restoring material in contact with the pretreatment material as well as the pretreatment material layer is unlikely to be completed. Therefore, the adhesion between the filling/restoring material and the pretreatment material has not become sufficient clinically, and further, the adhesion durability also tends to be poor.

In order to solve the above-mentioned problem, in the dental filling/restoration kit according the embodiment of the present invention, it is more preferred that a composite resin (A) further contain a tertiary amine compound (d) and a basic inorganic material (e) (hereinafter, the case where the composite resin does not contain the tertiary amine compound (d) and the basic inorganic material (e) will be referred to as a "first embodiment", and the case where the composite resin contains the tertiary amine compound (d) and the basic inorganic material (e) will be referred to as a "second embodiment").

In a second embodiment, because the composite resin does not have an acidic group, the neutralization reaction is not effected between the acidic group, and the tertiary amine compound and the basic inorganic material, before a cavity of a tooth is filled with the composite resin. Further, the composite resin contains the basic inorganic material in addition to the tertiary amine having a high effect of promoting the polymerization. Therefore, in the mixed layer of the primer and the composite resin, the basic inorganic material is neutralized, competing with the tertiary amine, after the filing of the composite resin, and the tertiary amine in the remaining portion that has not been subjected to the neutralization reaction can enhance the effect of promoting the polymerization of the photopolymerization initiator in the mixed layer of the primer and the composite resin. In particular, this effect becomes conspicuous in the case where the basic inorganic material to be used has a relatively high basicity, which is more preferred. Further, the composite resin does not contain a radical-polymerizable monomer having an acidic group and does not adsorb a basic material, and hence, the composite resin is further unlikely to be colored and is excellent in sensuousness.

(a) Radical-Polymerizable Monomer Having No Acidic Group

In the present embodiment, the composite resin contains a water-soluble radical-polymerizable monomer having no acidic group without fail as a radical-polymerizable monomer having no acidic group. As the radical-polymerizable monomer having no acidic group, a radical-polymerizable monomer having no acidic group other than the water-soluble radical-polymerizable monomer having no acidic group may be used together.

In the present embodiment, as the radical-polymerizable monomer having no acidic group, any compound having no acidic group in molecules of the radical-polymerizable monomer can be used without any limit. Specifically, the acidic group refers to a functional group capable of dissociating an active proton, having pKa smaller than 5, such as a phosphinico group, a phosphono group, a sulfo group, or a carboxyl group.

As such a radical-polymerizable monomer having no acidic group, a (meth)acrylate-based monomer is used mainly due to the satisfactory polymerization property. Specific examples of the (meth)acrylate-based monomer include the following (1) to (4).

(1) Monofunctional Radical-Polymerizable Monomer

Examples of the monofunctional radical-polymerizable monomer include alkyl esters of (meth)acrylates such as ethylhexyl(meth)acrylate, isodecyl(meth)acrylate, n-lauryl(meth)acrylate, tridecyl(meth)acrylate, n-stearyl(meth)acrylate, cyclohexyl(meth)acrylate, benzyl(meth)acrylate, phenoxyethyl(meth)acrylate, isobornyl(meth)acrylate, 2-hydroxyethyl(meth)acrylate, 3-hydroxypropyl(meth)acrylate, tetrahydrofurfuryl(meth)acrylate, and glycidyl(meth)acrylate; fluorine-containing (meth)acrylates such as 1H,1H,3H-hexafluorobutyl methacrylate, 1H,1H,5H-octafluoropentyl methacrylate, 1H,1H,6H-decafluorohexyl methacrylate, and 1H,1H,7H-dodecafluoroheptyl methacrylate; and (meth)acrylates represented by the following formulas (g) to (k), (p), and (q).

[Chem 1]

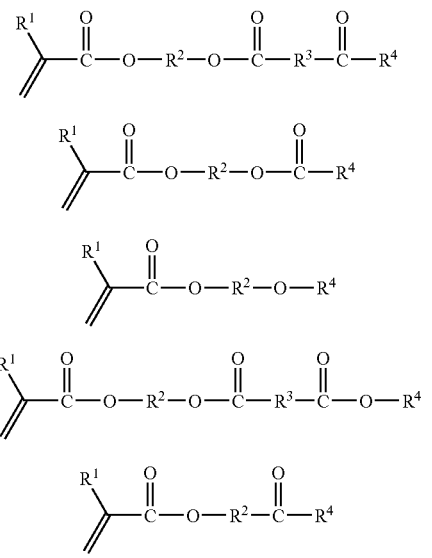

[Chem 2]

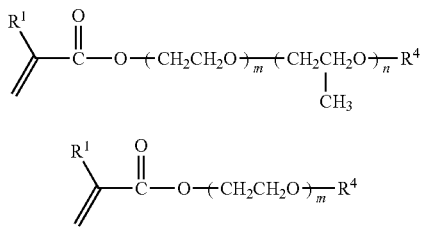

It should be noted that each of $R^1$'s in the above formulas is a hydrogen atom or a methyl group. Further, $R^2$'s and $R^3$'s in the above formulas independently represent an alkylene group. Further, each of $R^4$'s in the above formulas is an alkyl group. m in the above formulas is 0 or an integer of 1 to 10 and each of n's is an integer of 1 to 10 (provided that m+n is an integer of 2 to 10).

(2) Bifunctional Radical-Polymerizable Monomer

Examples of the bifunctional radical-polymerizable monomer include ethylene glycol di(meth)acrylate, diethylene glycol di(meth)acrylate, triethylene glycol di(meth)acrylate, butylene glycol di(meth)acrylate, neopentyl glycol di(meth)acrylate, propylene glycol di(meth)acrylate, 1,3-butanediol di(meth)acrylate, 1,4-butanediol di(meth)acrylate, 1,6-hexanediol di(meth)acrylate, 1,9-nonanediol di(meth)acrylate, 1,10-decanediol di(meth)acrylate, 2,2-bis((meth)acryloxyphenyl)propane, 2,2-bis[4-(3-(meth)acryloxy)-2-hydroxypropoxyphenyl]propane, 2,2-bis(4-(meth)acryloxyethoxyphenyl)propane, 2,2-bis(4-(meth)acryloxydiethoxyphenyl) propane, 2,2-bis(4-(meth)acryloxytetraethoxyphenyl) propane, 2,2-bis(4-(meth)acryloxypentaethoxyphenyl) propane, 2,2-bis(4-(meth)acryloxydipropoxyphenylpropane, 2-(4-methacryloxyethoxyphenyl)-2-(4-(meth)acryloxydiethoxyphenyl)propane, 2-(4-(meth)acryloxydiethoxyphenyl)-2-(4-(meth)acryloxytriethoxyphenyl)propane, 2-(4-(meth)acryloxydipropoxyphenyl-2-(4-(meth) acryloxytriethoxyphenyl)propane, 2,2-bis(4-(meth)acryloxypropoxyphenyl)propane, and 2,2-bis(4-(meth)acryloxyisopropoxyphenylpropane.

(3) Trifunctional Radical-Polymerizable Monomer

Examples of the trifunctional radical-polymerizable monomer include trimethylolpropane tri(meth)acrylate, trimethylolethane tri(meth)acrylate, pentaerythritol tri(meth)acrylate, and trimethylolmethane tri(meth)acrylate.

(4) Tetrafunctional Radical-Polymerizable Monomer

Examples of the tetrafunctional radical-polymerizable monomer include pentaerythritol tetra(meth)acrylate, ditrimethylolpropane tetra(meth)acrylate, and pentaerythritol hexa(meth)acrylate.

Further, of the above-mentioned radical-polymerizable monomers having no acidic group, radical-polymerizable monomers having two or more functional groups are preferred in terms of the mechanical strength.

In the present invention, the radical-polymerizable monomer as described above may be used alone or at least two kinds of radical-polymerizable monomers may be used together. Further, a plurality of kinds of radical-polymerizable monomers having different numbers of functional groups may be combined. In any case, it is necessary to use a water-soluble radical-polymerizable monomer having no acidic group without fail.

(a1) Water-Soluble Radical-Polymerizable Monomer Having No Acidic Group

A composite resin contained in the dental filling/restoration kit according to the present embodiment contains a water-soluble radical-polymerizable monomer having no acidic group as a radical-polymerizable monomer having no acidic group. In the present specification, the term "water-soluble" means that the solubility with respect to water at 23° C. is 1 g/l or more. More preferably, the solubility is 100 g/l or more. As such a water-soluble radical-polymerizable monomer having no acidic group, of the (meth)acrylate-based monomers having no acidic group, water-soluble (meth)acrylate-based monomers can be used without any limit. Specific example thereof include (meth)acrylate-based monomers having a hydroxyl group such as 2-hydroxyethyl(meth)acrylate or 3-hydroxypropyl(meth)acrylate, and methacrylates having an ethylene glycol chain in molecules, such as polyethylene glycol di(meth)acrylate and methoxypolyethylene glycol methacrylate. Those monomers can be used alone or in combination of at least two kinds.

Of the above-mentioned water-soluble radical-polymerizable monomers having no acidic group, it is preferred to use a polyfunctional radical-polymerizable monomer. Specifically, it is preferred to use a polyfunctional radical-polymerizable monomer such as polyethylene glycol di(meth)acrylate, rather than a monofunctional radical-polymerizable monomer such as 2-hydroxyethyl(meth)acrylate or 3-hydroxypropyl(meth)acrylate. The adhesive strength between the composite resin and the tooth, in particular, the dentin via a primer can be enhanced by using a polyfunctional radical-polymerizable monomer.

Examples of preferred water-soluble polyfunctional radical-polymerizable monomers include polyethylene glycol dimethacrylate having a polymerization degree of 9 to 30, dimethacrylate of polyethoxylated bisphenols in which the polymerization degree of a polyethylene glycol site is 20 to 50 in total, and a methacrylic acid adduct of mono- or polyethylene glycol diglycidyl ether, and of those, polyethylene glycol dimethacrylate and polyethoxylated bisphenol A dimethacrylate are more preferred. Of those, polyethylene glycol dimethacrylate can be used most preferably.

Further, in the case where the composite resin contains to 30 parts by mass of the above-mentioned water-soluble radical-polymerizable monomer having no acidic group based on 100 parts by mass of the radical-polymerizable monomer contained in the composite resin, the adhesive strength of the composite resin with respect to the dentin is enhanced via a primer. Further, when the composite resin contains 3 parts by mass or more of the water-soluble radical-polymerizable monomer having no acidic group, a polymerization initiator can move easily between the composite resin and the primer. Further, when the composite resin contains 30 parts by mass or less of the above-mentioned water-soluble radical-polymerizable monomer having no acidic group, the water absorbing properties can be decreased. Thus, in order to facilitate the movement of the polymerization initiator, suppress the water absorbing properties, and enhance the adhesive strength between the tooth and the composite resin, it is preferred that the composite resin contain 3 to 30 parts by mass of the water-soluble radical-polymerizable monomer having no acidic group based on 100 parts by mass of the radical-polymerizable monomer. The particularly preferred amount of the water-soluble radical-polymerizable monomer having no acidic group is 5 to 25 parts by mass based on 100 parts by mass of the radical-polymerizable monomer. Further, in order to increase the pH gradient between the composite resin and the primer, it is preferred to use a radical-polymerizable monomer having no acidic group as another radical-polymerizable monomer excluding the water-soluble radical-polymerizable monomer having no acidic group. Further, when the radical-polymerizable monomer having no acidic group is used as another radical-polymerizable monomer, the composite resin does not adsorb a basic substance, and hence, the composite resin is more unlikely to be colored and is excellent in sensuousness.

Further, as such a radical-polymerizable monomer having no acidic group, it is more preferred to use a water-insoluble radical-polymerizable monomer having no acidic group. This is because the water-insoluble radical-polymerizable monomer is unlikely to expand and shrink due to the water absorption.

Specific examples of the radical-polymerizable monomers having no acidic group include water-insoluble (meth)acrylate-based monomers having a polymerizable unsaturated group, such as methyl(meth)acrylate, ethyl(meth)acrylate, isopropyl(meth)acrylate, butyl(meth)acrylate, 2-ethylhexyl (meth)acrylate, glycidyl(meth)acrylate, benzyl(meth)acrylate, allyl(meth)acrylate, tetrahydrofurfuryl(meth)acrylate, 2-(meth)acryloxyethyl propionate, and 2-methacryloxyethyl acetoacetate; aliphatic (meth)acrylate-based monomers having a plurality of polymerizable unsaturated groups, such as ethylene glycol di(meth)acrylate, diethylene glycol di(meth)acrylate, triethylene glycol di(meth)acrylate, butylene glycol di(meth)acrylate, nona-ethylene glycol di(meth)acrylate, propylene glycol di(meth)acrylate, dipropylene glycol di(meth)acrylate, neopentyl glycol di(meth)acrylate, 1,3-butanedioldi(meth)acrylate, 1,4-butanedioldi(meth)acrylate, 1,6-hexanedioldi(meth)acrylate, 1,9-nonanedioldi(meth)acrylate, trimethylolpropane tri(meth)acrylate, neopentyl glycol di(meth)acrylate, pentaerythritol tri(meth)acrylate, trimethylolmethane tri(meth)acrylate, pentaerythritol tetra(meth)acrylate, and urethane(meth)acrylate; and aromatic (meth)acrylate-based monomers having a plurality of polymerizable unsaturated groups, such as 2,2-bis((meth)acryloxyphenyl) propane, 2,2-bis[4-(2-hydroxy-3-(meth)acryloxy)propoxyphenyl]propane, 2,2-bis(4-(meth)acryloxyethoxyphenyl)propane, 2,2-bis(4-(meth)acryloxydiethoxyphenyl)propane, 2,2-bis(4-(meth)acryloxytriethoxyphenyl)propane, and 2,2-bis(4-(meth)acryloxypropoxyphenyl)propane. Any one of them may be used alone, or two or more of them may be used in mixture.

(b) Photopolymerization Initiator

In the present embodiment, as a photopolymerization initiator contained in the composite resin, a photopolymerization initiator generating a radial, in which a compound itself is capable of being polymerized along with the light irradiation is preferably used. An example of such a photopolymerization initiator includes α-keto carbonyl compound or an acylphosphine oxide compound.

Examples of the α-keto carbonyl compound include α-diketone, α-ketoaldehyde, α-ketocarboxylic acid, and α-ketocarboxylate. Specifically, α-diketones such as diacetyl, 2,3-pentadione, 2,3-hexadione, benzyl, 4,4'-dimethoxybenzyl, 4,4'-diethoxybenzyl, 4,4'-oxybenzyl, 4,4'-dichlorobenzyl, 4-nitrobenzyl, α-naphthyl, β-naphthyl, camphorquinone, camphorquinone sulfonic acid, camphorquinone carboxylate, and 1,2-cyclohexanedione; α-ketoaldehydes such as methylglyoxal and phenylglyoxal; pyruvic acid, benzoylformatic acid, phenylpyruvic acid, methyl pyruvate, ethyl benzoylformate, methyl phenylpyruvate, and butyl phenylpyruvate.

Of those α-ketocarbonyl compounds, in terms of stability and the like, α-diketones are preferably used. Of the α-diketones, diacetyl, benzyl, and camphorquinone are particularly preferable.

Examples of the acylphosphine oxide compound include benzoyl dimethoxyphosphine oxide, benzoyl ethoxyphenylphosphine oxide, benzoyl diphenylphosphine oxide, 2-methylbenzoyl diphenylphosphine oxide, and 2,4,6-trimethylbenzoyl diphenylphosphine oxide, bis(2,6-dimethoxybenzoyl)-2,4,4-trimethylpentylphosphine oxide, and bis(2,4,6-trimethylbenzoyl)-phenylphosphine oxide.

It is more preferred to set the blending amount of the photopolymerization initiator to be in a range of 0.01 to 5 parts by mass with respect to 100 parts by mass of the radical-polymerizable monomer having no acidic group in the composite resin.

Further, particularly in the second embodiment, of those photopolymerization initiators, it is particularly preferred to use an acylphosphine oxide compound that exhibits the effect of promoting the polymerization with a tertiary amine compound as a polymerization promoter and has, in itself, the sufficiently high effect of initiating the polymerization. Further, in the second embodiment, it is more preferred to set the blending amount of the photopolymerization initiator to be in a range of 0.01 to 5 parts by mass with respect to 100 parts by mass of the radical-polymerizable monomer having no acidic group in the composite resin.

Further, in order to enhance the effect of initiating the polymerization of the photopolymerization initiator, a reducing compound that does not adversely influence the catalytic effect of the compound can also be used. In particular, in the case of using an α-keto carbonyl compound, it is preferred to enhance the effect of initiating the polymerization with a reducing compound to promote the photopolymerization.

As reducing compounds, tertiary amines which are also polymerization promoters are generally used. Specific examples of such tertiary amines include N,N-dimethylaniline, N,N-diethylaniline, N,N-di-n-butylaniline, N,N-dibenzylaniline, N,N-dimethyl-p-toluidine, N,N-diethyl-p-toluidine, N,N-dimethyl-m-toluidine, p-bromo-N,N-dimethylaniline, m-chloro-N,N-dimethylaniline, p-dimethylamino benzaldehyde, p-dimethylamino acetophenone, p-dimethylamino benzoate, ethyl p-dimethylaminobenzoate, amyl p-dimethylaminobenzoate, methyl N,N- dimethylanthranilate, N,N-dihydroxyethylaniline, N,N-dihydroxyethyl-p-toluidine, p-dimethylaminophenethyl alcohol, p-dimethylaminostilbene, N,N-dimethyl-3,5-xylidine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate, and 2,2'-(n-butylimino)diethanol. The reducing compound is generally added in an amount in a range of 0.1 to 10 times, more preferably 0.3 to 5 times that of the photopolymerization initiator to be used.

However, tertiary amine exhibits weak basicity in most cases, and hence, the tertiary amine may effect a neutralization reaction to form a salt when entering a primer that exhibits acidity from the composite resin. Then, particularly in the first embodiment, the effect of initiating the polymerization of the tertiary amine that has formed a salt may be degraded remarkably. Thus, in the first embodiment, as the photopolymerization initiator, it is particularly preferred to use an acylphosphine oxide compound having the sufficiently high effect of initiating the polymerization even without using a basic reducing compound.

Further, if a photoacid generator is combined with the photopolymerization initiator in the dental filling/restoration kit according to the present embodiment, the polymerization activity can be enhanced more. As the photoacid generator, those which generate Bronsted acid or Lewis acid by irradiation with light are used preferably.

Examples of the photoacid generators include halomethyl group-substituted-s-triazine derivatives, diaryliodonium salt compounds, sulfonium salt compounds, and pyridinium salt compounds. Of those photoacid generators, halomethyl group-substituted-s-triazine derivatives and diaryliodonium salt compounds are preferably used.

Examples of the halomethyl group-substituted-s-triazine derivatives include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-(p-methoxyphenyl)-4,6-bis(trichloromethyl)-s-triazine, 2-n-propyl-4,6-bis(trichloromethyl)-s-triazine, 2-(α,α,β-trichloroethyl)-4,6-bis(trichloromethyl)-s-triazine, 2-styryl-4,6-bis(trichloromethyl)-s-triazine, 2-(p-methoxystyryl)-4,6-bis(trichloromethyl)-s-triazine, 2-(o-methoxystyryl-4,6-bis(trichloromethyl)-s-triazine, 2-(p-butoxystyryl)-4,6-bis(trichloromethyl)-s-triazine, 2-(3,4-dimethoxystyryl)-4,6-bis(trichloromethyl)-s-triazine, and 2-(3,4,5-trimethoxystyryl)-4,6-bis(trichloromethyl)-s-triazine.

Further, examples of the diaryliodonium salt compounds include chlorides such as diphenyliodonium, bis(p-chlorophenyl)iodonium, ditolyliodonium, bis(p-tert-butylphenyl)iodonium, bis(m-nitrophenyl)iodonium, p-tert-butylphenylphenyliodonium, methoxyphenylphenyliodonium, p-octyloxyphenylphenyliodonium, 4-isopropylphenyl-4-methylphenyliodonium; and bromide, tetrafluoroborate, hexafluorophosphate, hexafluoroarsenate, hexafluoroantimonate, tetrakis(pentafluorophenyl)borate, trifluoromethanesulfonate. In particular, from the viewpoint of compound solubility, tetrafluoroborate, hexafluorophosphate, hexafluoroarsenate, hexafluoroantimonate, trifluoromethanesulfonate, and tetrakis(pentafluorophenyl)borate salts are preferably used.

The photoacid generator may be used alone or in combination of at least two kinds. Although the blending amount of these photoacid generators is not particularly limited as long as it is within the range in which they express the effect, the blending amount is preferably 0.001 to 12 parts by weight, more preferably 0.005 to 6 parts by weight based on 100 parts by weight of the radical-polymerizable monomer contained in the composite resin.

Further, in the dental filling/restoration kit of the present invention, high adhesive strength is obtained by only one irradiation with light even without allowing a polymerization initiator to be contained in a primer. However, a polymerization initiator or a reducing compound may be contained in both the composite resin and the primer. Even in the case where the polymerization initiator is contained in both the composite resin and the primer, the compound similar to the above can be used as the photopolymerization initiator. Further, the blending amount thereof is 0.01 to 5 parts by mass based on 100 parts by mass of the radical-polymerizable monomer in the primer.

(c) Filler

In the present embodiment, a filler contained in the composite resin is added for the purpose of enhancing the strength of the composite resin and to suppress the shrinkage thereof during the polymerization. Further, the viscosity (operability) of the composite resin before curing can be adjusted by the addition amount of the filler. The filler is contained in an amount of 80 to 2,000 parts by mass based on 100 parts by mass of the radical-polymerizable monomer contained in the composite resin. The particularly preferred amount of the filler is 90 to 500 parts by mass based on 100 parts by mass of the radical-polymerizable monomer contained in the composite resin, and the most preferred amount is 100 to 230 parts by mass. Further, in the case where the amount of the filler is less than 80 parts by mass, the sufficient strength of the composite resin is not obtained. In the case where the amount of the filler is larger than 2,000 parts by mass, the viscosity of the composite resin becomes too high, which degrades the operability for filling the composite resin. Further, it is more preferred to add the filler also to the primer, because the adhesive strength becomes larger.

In the present embodiment, as the filler, at least one kind can be selected from an inorganic filler, an organic filler, and an inorganic-organic complex filler. Further, in the second embodiment, as the inorganic filler, a basic inorganic material described later is used without fail.

Specific examples of the organic fillers which may be used in the present invention include non-cross-linked polymers such as polymethyl(meth)acrylate, polyethyl(meth)acrylate, a methyl(meth)acrylate/ethyl(meth)acrylate copolymer, a methyl(meth)acrylate/butyl(meth)acrylate copolymer, and a methyl(meth)acrylate/styrene copolymer; and (meth)acrylate polymers such as a methyl(meth)acrylate/ethylene glycol di(meth)acrylate copolymer, a methyl(meth)acrylate/triethylene glycol di(meth)acrylate copolymer, and copolymers of methyl(meth)acrylate with a butadiene-based monomer. Further, a mixture of two or more kinds of those may also be used.

As the kinds of the inorganic filler to be used in the present invention, those which are known can be selected to be used appropriately. Examples thereof include the first, second, third, and fourth groups of the periodic table; transition metals, and an oxide, a hydroxide, a chloride, a sulfate, a sulfite, a carbonate, a phosphate, and a silicate thereof; and a mixture or a composite salt thereof.

Typical specific examples of the inorganic filler include quartz, silica, alumina, silica titanium, silica zirconia, lanthanum glass, barium glass, and strontium glass. Further, cation-eluting fillers such as hydroxides (e.g., calcium hydroxide, strontium hydroxide) and oxides (e.g., zinc oxide, silicate glass, fluoroaluminosilicate glass) can also be used preferably. In particular, polyvalent metal ions eluted from fluoroaluminosilicate glass can enhance the adhesiveness with respect to a dentin and the physical properties of a cured body by being ion crosslinked with a polymer of a radical-polymerizable monomer having an acidic group.

Of the above-mentioned inorganic fillers, inorganic fillers made of metal oxide particles such as silica, alumina or zirconia, or complex metal oxide particles such as silica-titania or silica-zirconia can be used preferably. Further, these inorganic filers can be used in combination of at least two kinds.

The inorganic filler, which also has a function as a basic inorganic material used in the second embodiment, can also be used.

The inorganic filler having such a function is obtained by mixing distilled water and ethanol in a volume ratio of 1:1 as described later, adjusting the pH of the mixture to 2.50±0.03 with phosphoric acid, dispersing 1.0 g of a basic inorganic compound in 20 g of the resultant solution, followed by stirring for 2 minutes, thereby obtaining a dispersion whose pH value at 23° C. exhibits a pH differential value higher by 0.05 or more compared with the one having no basic inorganic compound. At this time, as the inorganic filler other than the basic inorganic compound to be used in combination with the basic inorganic compound, the inorganic filler having no strong acid point on the surface is used preferably. This is because the inorganic filler having a strong acid point on the surface may adsorb a tertiary amine compound.

Therefore, as the inorganic filler used in this case, an inorganic filler can be used preferably, which does not exhibit a violet color, using 4-phenylazodiphenylamine as an acid-base indicator, in anhydrous toluene.

Herein, although the measurement of the above-mentioned acid point using 4-phenylazodiphenylamine may be conducted in accordance with a routine procedure, the measurement is generally conducted by the following method. More specifically, first, a filler is dried at 100° C. for 3 or more hours and stored in a desicator containing diphosphorus pentoxide. One gram of the resultant filler is placed in a sample tube, and then, 3 g of anhydrous toluene is placed, followed by shaking vigorously, whereby the anhydrous toluene is dispersed so as not to form an aggregate. After the dispersion, one drop (about 0.016 g) of an anhydrous toluene solution of 0.004 mol/l of 4-phenylazodiphenylamine stored under shading is added to the sample tube, followed by shaking similarly, and thereafter, a violet color may be determined by visual inspection.

An inorganic-organic complex filler can also be used preferably. For example, a polymerizable monomer is previously added to an inorganic filler to obtain a paste, and the paste is polymerized and crushed, whereby a particulate organic-inorganic complex filler can be obtained. As the organic and inorganic complex filler, for example, a TMPT filler (obtained by mixing trimethylolpropane methacrylate and a silica filler, followed by polymerization and crushing) or the like can be used.

When the inorganic filler or the inorganic-organic complex filler is treated with a surface treatment agent such as a silane coupling agent, the affinity with a polymerizable monomer, and the dispersibility in the polymerizable monomer, and the mechanical strength and water resistance of a cured body can be enhanced. There is no particular limit to the surface treatment agent and the surface treatment method, and known methods can be adopted without any limit. Preferable examples of the silane coupling agents that may be used for the surface treatment of an inorganic filler include methyltrimethoxysilane, methyltriethoxysilane, methyltrichlorosilane, dimethyldichlorosilane, trimethylchlorosilane, vinyltrichlorosilane, vinyltriethoxysilane, vinyltris(β-methoxyethoxy) silane, γ-methacryloyloxypropyltrimethoxysilane, γ-chloropropyltrimethoxysilane, γ-glycidoxypropyltrimethoxysilane, and hexamethyldisilazane. Further, in addition to the silane coupling agents, surface treatment of inorganic fillers and inorganic/organic complex fillers may be performed by methods using titanate-based coupling agents, aluminate-based coupling agents, or zirco-aluminate-based coupling agents, or methods in which the polymerizable monomer is graft polymerized onto the surface of a filler particle.

The refractive index of the filler is not particularly limited. Thus, for general dental applications, fillers with a refractive index in a range of 1.4 to 2.2 are used preferably. Further, there is no particular limit to the shape or the particle size. Although the shape or particle size are selected to be used appropriately, it is preferred that an average particle size be generally 0.001 to 100 μm, particularly 0.001 to 10 μm. Further, of the above fillers, it is preferred to use a spherical inorganic filler, because the surface lubricative property of a cured body to be obtained increases to obtain an excellent restoring material.

(d) Tertiary Amine Compound

In the second embodiment, the composite resin contains a tertiary amine compound (d). By combining the tertiary amine compound (d) as a polymerization promoter with the photopolymerization initiator, the effect of promoting the polymerization of the photopolymerization initiator can be enhanced. In the second embodiment, any known tertiary amine compounds may be used as long as they function as a polymerization promoter.

In general, such tertiary amine compounds are roughly classified into aromatic tertiary amine compounds in which an aromatic group is bonded to a nitrogen atom, and aliphatic tertiary amine compounds in which only an aliphatic group is bonded.

(d1) Aliphatic Tertiary Amine Compound

An aliphatic tertiary amine compound is preferably used for dental purposes in terms of the relatively low volatility and no generation of odor. In the second embodiment, specific examples of the aliphatic tertiary amine compounds include aliphatic tertiary amine compounds such as triethylamine, tributylamine, triallylamine, N,N-dimethylaminoethyl methacrylate, N,N-diethylaminoethyl methacrylate, N-methyldiethanolamine, N-ethyldiethanolamine, N-propyldiethanolamine, N-ethyldiallylamine, N-ethyldibenzylamine, dimethylethanolamine, diethylethanolamine, dipropylethanolamine, triethanolamine, tri(isopropanol)amine, tri(2-hydroxybutyl)amine, and tribenzylamine.

Of the above-mentioned aliphatic tertiary amine compounds, from the viewpoint of ease of availability and synthesis, chemical stability of the compound, and excellent solubility in the polymerizable monomers, it is preferable to use N,N-dimethylaminoethyl methacrylate, N,N-diethylaminoethyl methacrylate, N-methyldiethanolamine, N-ethyldiethanolamine, N-propyldiethanolamine, N-ethyldiallylamine, N-ethyldibenzylamine, dimethylethanolamine, diethylethanolamine, triethylamine, triethanolamine, and tributylamine are preferably used. Of those, N,N-dimethylaminoethyl methacrylate, dimethylethanolamine, and triethanolamine are particularly preferably used.

(d2) Aromatic Tertiary Amine Compound

In the second embodiment, a typical aromatic tertiary amine compound refers to an amine compound in which at least one aromatic group and at most two aliphatic groups are bonded to a nitrogen atom of an amino group. In the second embodiment, as the typical aromatic tertiary amine compound, those which are known can be used without any particular limit. In particular, those which are represented by the following General Formula (3) are preferably used in terms of the easy availability.

[Chem 3]

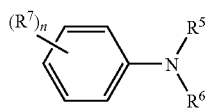

General Formula (3)

In General Formula (3), $R^5$ and $R^6$ are respectively and independently an alkyl group; $R^7$ is an alkyl group, an aryl group, an alkenyl group, an alkoxy group, a cyano group, a carbonyl group, an aminocarbonyl group, or an alkyloxycarbonyl group. Further, n is an integer of 0 to 5. In the case where n is 2 or more, a plurality of $R^7$'s may or may not be the same. Further, $R^7$'s may be combined with each other to form a ring.

The alkyl group in $R^5$, $R^6$, and $R^7$ preferably has 1 to 6 carbon atoms, and examples of the alkyl group include a methyl group, an ethyl group, an n-propyl group, an i-propyl group, an n-butyl group, and an n-hexyl group. Further, needless to say, the alkyl group may be a substituted alkyl group having a substituent, and examples of such a substituted alkyl group include a halogen substituted alkyl group such as a fluoromethyl group and 2-fluoroethyl group, or a hydroxyl substituted alkyl group such as a 2-hydroxyethyl group.

Further, any of the aryl group, alkenyl group, alkoxy group, cyano group, carbonyl group, aminocarbonyl group, or alkyloxycarbonyl group in $R^7$ may have a substituent. Examples of the aryl group include a phenyl group, a p-methoxyphenyl group, a p-methylthiophenyl group, a p-chlorophenyl group, and a 4-biphenylyl group each having 6 to 12 carbon atoms. Examples of the alkenyl group include a vinyl group, a propenyl group, and a 2-phenylethenyl group each having 2 to 12 carbon atoms. Examples of the alkoxy group include a methoxy group, an ethoxy group, and a butoxy group each having 1 to 10 carbon atoms; examples of the carbonyl group include a formyl group, an acetyl group, a propionyl group, and a benzoyl group; examples of the aminocarbonyl group include an aminocarbonyl group, a methylaminocarbonyl group, and dimethylaminocarbonyl group; and examples of the alkyloxycarbonyl group include a methoxycarbonyl group, an ethoxycarbonyl group, a butoxycarbonyl group, an amyloxycarbonyl group, and an isoamyloxycarbonyl group in each of which an alkyloxy group has 1 to 10 carbon atoms.

In the aromatic tertiary amine represented by General Formula (3) above, an alkyl group having 1 to 6 carbon atoms is preferred as $R^5$ and $R^6$. In particular, a unsubstituted alkyl group (e.g., a methyl group, an ethyl group, an n-propyl group) having 1 to 3 carbon atoms or a 2-hydroxyethyl group are more preferred. Of those, the methyl group is more preferred.

Further, in the case where n=1, the bonding position of $R^7$ is preferably a para-position. In particular, $R^7$ is preferably an alkyl group or an alkyloxycarbonyl group, and an alkyloxycarbonyl group is most preferred. On the other hand, in the case where 2 to 3 $R^7$'s are bonded, the bonding position is preferably an ortho-position and/or a para-position. In particular, the case where n=1 is more preferred.

The aromatic tertiary amine compound represented by General Formula (3) will be illustrated specifically. Examples of a compound that is an alkyloxycarbonyl group in which $R^7$ is bonded to a para-position include a methyl p-dimethylaminobenzoate, an ethyl p-dimethylaminobenzoate, a propyl p-dimethylaminobenzoate, an amyl p-dimethylaminobenzoate, an isoamyl p-dimethylaminobenzoate, an ethyl p-diethylaminobenzoate, and a propyl p-diethylaminobenzoate. Further, specific examples of other aromatic amine compounds include N,N-dimethylaniline, N,N-dibenzylaniline, N,N-dimethyl-p-toluidine, N,N-diethyl-p-toluidine, N,N-di (β-hydroxyethyl)-p-toluidine, N,N,2,4,6-pentamethylaniline, N,N,2,4-tetramethylaniline, N,N-diethyl-2,4,6-trimethylaniline, N,N-dimethylacetophenone, N,N-dimethylcyanobenzene, a p-diethylaminobenzoic acid, and an amide p-dimethylaminobenzoate. Of those, the ethyl p-diethylaminobenzoate or the N,N-dimethyl-p-toluidine are particularly preferably used, and the ethyl p-dimethylaminobenzoate is most preferred.

These tertiary amine compounds may be used alone, if required, or in combination of at least two kinds of compounds.

Of those, an amine compound in which a pKa value of the corresponding ammonium ions in water at 25° C. is 9 or less is preferably used in terms of the difficulty in a neutralization reaction with an acidic group of a radical-polymerizable monomer having an acidic group contained in the primer described later and the relatively low acidity, and in particular, amine having the pKa value of 7.0 or less is preferably used. Amine with such a low basicity is generally an aromatic tertiary amine, and when at last one of those illustrated above is used, the effect of promoting the polymerization of the photopolymerization initiator inside both the primer and composite resin described later at a contact interface therebetween and in the vicinity thereof can be enhanced.

In the second embodiment, generally, the tertiary amine compound is typically added in a range of the weight of 0.1 to 10 times that of the photopolymerization initiator to be used. More preferably 0.01 to 10 parts, and particularly preferably 0.02 to 5 parts by mass of the tertiary amine compound is added based on the total 100 parts by mass of the radical-polymerizable monomer having no acidic group in the composite resin.

(e) Basic Inorganic Material

In the second embodiment, the basic inorganic material contained in the composite resin is added for the purpose of enhancing the strength of the composite resin and enhancing the effect of promoting the polymerization of the tertiary amine compound at a time of polymerization. The basic inorganic material is generally contained in an amount of 3 parts by mass or more based on 100 parts by mass of the radical-polymerizable monomer having no acidic group contained in the composite resin. The particularly preferred amount of the basic inorganic material is 5 to 80 parts by mass based on 100 parts by mass of the radical-polymerizable monomer contained in the composite resin, and 8 to 30 parts by mass is most preferred. In the case where the amount of the basic inorganic material is 3 parts by mass or more, the sufficient effect of promoting the polymerization of the tertiary amine compound during polymerization is obtained.

The basic inorganic material in the second embodiment is obtained by mixing distilled water and ethanol in a volume ratio of 1:1, adjusting the pH of the mixture to 2.50±0.03 with phosphoric acid, dispersing 1.0 g of a basic inorganic compound in 20 g of the resultant solution, followed by stirring for 2 minutes, thereby obtaining a dispersion whose pH value at 23° C. exhibits a pH differential value higher by 0.05 or more compared with the one having no basic inorganic compound. The pH may be measured with a pH meter, using a glass electrode utilizing a potassium chloride solution.

In the second embodiment, the basic inorganic material contained in the composite resin also functions as a filler.

Therefore, in the second embodiment, the filling/restoring material (A)″ contains 100 parts by mass of a radical-polymerizable monomer (a) containing 3 to 30 parts by mass of a water-soluble radical-polymerizable monomer having no acidic group (a1), a photopolymerization initiator (b), 80 to 2,000 parts by mass of a filler (c), a tertiary amine compound (d), and a basic inorganic material (e)″, and specifically, is roughly classified into the following two kinds.

<First Filling/Restoring Material>

The first filling/restoring material contains 100 parts by mass of a radical-polymerizable monomer (a) containing 3 to 30 parts by mass of a water-soluble radical-polymerizable monomer having no acidic group (a1), a photopolymerization initiator (b), a tertiary amine compound (d), and 80 to 2,000 parts by mass of a basic inorganic material.

<Second Filling/Restoring Material>

The second filling/restoring material contains 100 parts by mass of a radical-polymerizable monomer (a) containing 3 to 30 parts by mass of a water-soluble radical-polymerizable monomer having no acidic group (a1), a photopolymerization initiator (b), a tertiary amine compound (d), and 80 to 2,000 parts by mass of a mixed filler formed of at least one kind of a filler selected from an inorganic filler, an organic filler, and an inorganic-organic complex filler, excluding a basic inorganic material, and a basic inorganic material.

In the second filling/restoring material, the ratio of the basic inorganic material occupying the mixed filler components is preferably 0.5% by mass or more to 70% by mass or less, and more preferably 1.0% by mass or more to 50% by mass or less. By setting the ratio of the basic inorganic material occupying the mixed filler components to be 0.5% by mass or more, the effect of promoting the polymerization of the tertiary amine compound during polymerization can be ensured exactly.

There is no particular limit to the inorganic compound that can be used as a basic inorganic material, as long as the above conditions are satisfied. However, the inorganic compound can be selected from an oxide, a hydroxide, a fluoride, a carbonate, and a silicate of the first, second, and third groups, and a mixture or a complex salt thereof. The pH differential value is more preferably 0.10 to 4.50, and particularly preferably 0.15 to 1.00 in terms of the storage stability. Further, in terms of the adhesive strength, an inorganic basic material capable of eluting divalent or higher polyvalent metal ions is preferred, and a basic inorganic material capable of eluting trivalent or more polyvalent metal ions is most preferred.

Specific examples of typical basic inorganic materials include oxides such as alumina, calcia, and magnesia. Further examples include hydroxides such as calcium hydroxide, magnesium hydroxide, and strontium hydroxide, fluorides such as sodium fluoride and calcium fluoride, and carbonates such as calcium carbonate, magnesium carbonate, and strontium carbonate. Further examples include silicates such as calcium silicate, aluminum silicate, fluoroaluminosilicate glass, and other silicate glass. Of those, basic inorganic materials eluting metal ions such as a calcium ion and an aluminum ion may be suitably used. In particular, the basic inorganic materials eluting trivalent or more metal ions are preferred, and of those, fluoroaluminosilicate glass is used most preferably. This is because the polyvalent metal ions eluted from the fluoroaluminosilicate glass can enhance the adhesiveness with a dentin and the physical properties of a cured body by being ion crosslinked with a polymer of a radical-polymerizable monomer having an acidic group.

Any known fluoroaluminosilicate glass including a cement for dental use such as a fluoroaluminosilicate glass for a glass ionomer cement may be suitably used for the above-mentioned fluoroaluminosilicate glass. The composition of generally known fluoroaluminosilicate glass, which is suitably used, is, in terms of ion mass percent, 10 to 33 of silicon; 4 to 30 of aluminum; 5 to 36 of alkali earth metals; 0 to 10 of alkali metals; 0.2 to 16 of phosphorus; 2 to 40 of fluorine; and oxygen, the balance. Examples of a more preferable composition range are, 15 to 25 of silicon; 7 to 20 of aluminum; 8 to 28 of alkali earth metals; 0 to 10 of alkali metals; 0.5 to 8 of phosphorus; 4 to 40 of fluorine; and oxygen, the balance. A compound in which a part or all of the calcium is substituted with magnesium, strontium, or barium is preferable. Further, although sodium is the most typical of the alkali metals, a compound in which a part or all of the sodium is substituted with lithium or potassium is also suitable. Further, as required, a part of the aluminum may be substituted with yttrium, zirconium, hafnium, tantalum, lanthanum, or the like.

There is no particular limit to the shape of the basic inorganic compound that can be used in the second embodiment. Crushed particles obtained by ordinary crushing or spherical particles may be used, and if required, particles in a plate shape, a fiber shape, or the like can also be mixed.

Further, the basic inorganic compound has an average particle size of preferably 0.01 µm to 20 µm, more preferably 0.05 µm to 15 µm, and still more preferably 0.1 µm to 5 µm, because the neutralization reaction with a radical-polymerizable monomer having an acidic group in the primer described later is accelerated and the operability is not degraded.

When the basic inorganic material is treated with a surface treatment agent such as a silane coupling agent, the affinity with a polymerizable monomer, the dispersibility in the polymerizable monomer, and the mechanical strength and water resistance of a cured body can be enhanced. There is no particular limit to the surface treatment agent and the surface treatment method, and known methods can be adopted without any limit. Preferable examples of the silane coupling agents that may be used for the surface treatment of the basic inorganic material include methyltrimethoxysilane, methyltriethoxysilane, methyltrichlorosilane, dimethyldichlorosilane, trimethylchlorosilane, vinyltrichlorosilane, vinyltriethoxysilane, vinyltris(β-methoxyethoxy)silane, γ-methacryloyloxypropyltrimethoxysilane, γ-chloropropyltrimethoxysilane, γ-glycidoxypropyltrimethoxysilane, and hexamethyldisilazane. Further, in addition to the silane coupling agents, surface treatment of the basic inorganic material can be performed by methods using titanate-based coupling agents, aluminate-based coupling agents, or zirco-aluminate-based coupling agents, or methods in which the polymerizable monomer is graft polymerized onto the surface of a filler particle.

(f) Radical-Polymerizable Monomer Having an Acidic Group

As the radical-polymerizable monomer having an acidic group contained in a primer of a dental filling/restoration kit according to the present embodiment, known compounds can be used without any particular limit, as long as they have at least one acidic group and one radical-polymerizable unsaturated group in one molecule. The radical-polymerizable monomer having an acidic group is contained preferably in an amount of 10 parts by mass or more based on 100 parts by mass of the radical-polymerizable monomer contained in a primer, and the radical-polymerizable monomer having an acidic group is contained more preferably in an amount of 30 parts by mass or more based on 100 parts by mass of the radical-polymerizable monomer contained in the primer. Further, examples of the acidic group include a carboxyl group, a sulfo group, a phosphon group, a monoester phosphate group, or a diester phosphate group. Of those, as an acidic group having high adhesiveness with a dentin, a carboxyl group, a monoester phosphate group, or a diester phosphate group is more preferred. Further, it is most preferred that the acidic group of the radical-polymerizable monomer having an acidic group contained in a primer is strongly acidic so as to set the pH gradient between the composite resin and the primer to be more steep for the purpose of activating the movement of materials between the composite resin and the primer. As such an acidic group that is strongly acidic, a monoester phosphate group or a diester phosphate group is most preferred.

Specific examples of the radical-polymerizable monomers having an acidic group include carboxylic acidic radical-polymerizable monomers such as 2-(meth)acroyloxyethylhydrogen maleate, 2-(meth)acroyloxyethylhydrogen succinate, 2-(meth)acroyloxyethylhydrogen phthalate, 11-(meth)acroyloxyethyl-1,1-undecanedicarboxylic acid, 2-(meth)acroyloxyethyl-3'-methacroyloxy-2'-(3,4-dicarboxybenzoyl oxy)propyl succinate, 4-(2-(meth)acroyloxyethyl)trimellitate anhydride, N-(meth)acroylglycine, and N-(meth)acroylasparaginic acid; radical-polymerizable monomers having a phosphoric acid acidic group such as 2-(meth)acryloyloxyethylphenylhydrogen phosphate, bis((meth)acryloyloxyethyl)hydrogen phosphate, (meth)acryloyloxyethyldihydrogen phosphate, 10-(meth)acryloyloxydecyldihydrogen phosphate, and 6-(meth)acryloyloxyhexyldihydrogen phosphate; radical-polymerizable monomers having a phosphonic acid acidic group such as vinyl phosphonic acid; and radical-polymerizable monomers having a sulfonic acid acidic group such as styrene sulfonic acid, 3-sulfopropane(meth)acrylate, and 2-(meth)acrylamide-2-methylpropanesulfonic acid. Further, as required, two or more of the radical-polymerizable monomers having an acidic group may be used in combination.

The primer may contain a monomer having no acidic group in addition. As the polymerizable monomer having no acidic group, the water-soluble radical-polymerizable monomer having no acidic group described above, or a water-insoluble radical-polymerizable monomer having no acidic group can be used. In particular, it is preferred that the water-soluble radical-polymerizable monomer having no acidic group be contained in the primer, because the permeability of the primer with respect to a dentin and the compatibility of the water-insoluble radical-polymerizable monomer having no acidic group with respect to water are enhanced. On the other hand, it is preferred that the water-insoluble radical-polymerizable monomer having no acidic group be contained in the primer, because the strength of a cured primer layer is enhanced. However, the phase separation occurs between the polymerizable monomer and the water, which may hinder the entry of the polymerization initiator from the composite resin.

Therefore, the water-insoluble radical-polymerizable monomer having no acidic group is contained in the primer preferably in an amount of 5 parts by mass or less based on 100 parts by mass of the radical-polymerizable monomer, and in the case where the water-insoluble radical-polymerizable monomer having no acidic group is contained in the primer in an amount of more than 5 parts by mass, it is preferred to use it together with the water-soluble radical-polymerizable monomer having no acidic group.

(g) Water

The water contained in the primer of the dental filling/restoration kit according to the present embodiment has a function of assisting in the decalcification of a dentin by the radical-polymerizable monomer having an acidic group. The water is contained in the primer preferably in an amount of 5 to 150 parts by mass based on 100 parts by mass of the radical-polymerizable monomer contained in the primer, and in particular, the water is contained in the primer more preferably an in amount of 15 to 110 parts by mass based on 100 parts by mass of the radical-polymerizable monomer contained in the primer.

In order to further enhance the operability of the primer, the primer may contain a hydrophilic organic solvent having flowability. For example, the primer may contain a solvent such as acetone, ethanol, or isopropyl alcohol. In particular, a solvent with high volatility and low toxicity such as ethanol or isopropyl alcohol is used preferably, because such a solvent facilitates the drying described later.

The content of the hydrophilic organic solvent is preferably 20 to 400 parts by mass based on 100 parts by mass of the radical-polymerizable monomer contained in the primer, and the more preferred content of the hydrophilic organic solvent is 50 to 300 parts by mass based on 100 parts by mass of the radical-polymerizable monomer contained in the primer.

Further, in the case where the present embodiment is an embodiment other than the second embodiment, the content of the hydrophilic organic solvent is preferably 20 to 300 parts by mass based on 100 parts by mass of the radical-polymerizable monomer contained in the primer, and the more preferred content of the hydrophilic organic solvent is 50 to 150 parts by mass based on 100 parts by mass of the radical-polymerizable monomer contained in the primer.

Further, the primer may contain a filler so as to enhance the strength of the cured primer layer. For example, the primer may contain the above-mentioned inorganic filler, organic filler, or inorganic-organic complex filler. Of those, it is preferred to use the non-basic inorganic filler. The content of the filler is preferably 0.5 to 30 parts by mass based on 100 parts by mass of the radical-polymerizable monomer contained in the primer, and the more preferred content of the filler is 1 to 30 parts by mass based on 100 parts by mass of the radical-polymerizable monomer contained in the primer.

In the present embodiment, it is preferred that a vanadium compound be blended in the primer, and a hydroperoxide that is an organic peroxide be blended in the composite resin.

The vanadium compound used in the primer in the present embodiment is +IV-valent and/or +V-valent vanadium compound. By compounding the +IV-valent and/or +V-valent vanadium compound in the primer, a radical polymerization reaction is effected between the radical-polymerizable monomer having an acidic group in the primer and the hydroperoxide that is an organic peroxide in the composite resin described later at an adhesion interface between the composite resin and the primer and in the inside thereof, whereby the adhesiveness between the composite resin and the primer can be made very satisfactory.

The oxidation number of the vanadium compound is a valence of −I to a valence of +V, but for the vanadium compound to be used in the present invention, in terms of high stability and activation, it is particularly preferable to use a +IV-valent or +V-valent vanadium compound. As the +IV-valent or +V-valent vanadium compound, any known compound may be used without limitation. Specific examples include vanadium compounds such as divanadium tetraoxide (IV), vanadium oxide acetylacetonate (IV), oxalic acid vanadyl (IV), vanadyl sulfate (IV), oxobis(1-phenyl-1,3-butanedionate)vanadium (IV), oxovanadium (IV) bismaltolato, vanadium pentoxide (V), sodium methavanadate (V), methavanadate ammonium (V), and vanadium (V) oxytriisopropoxide. Of those, from the viewpoint of solubility in the primer, vanadium oxide acetylacetonate (IV), oxovanadium (IV) bismaltolato, and vanadium (V) oxytriisopropoxide are preferable, and oxovanadium (IV) bismaltolato is most preferable.

A plurality of kinds of these +IV-valent or +V-valent vanadium compounds may be used together. Hereinafter, for convenience, the vanadium compound will refer to the +IV-valent or +V-valent vanadium compound.

The blending amount of the vanadium compound in the primer of the present embodiment is not particularly limited. It is preferred that the blending amount be larger in order to obtain high adhesiveness, while the storage stability is excellent in a smaller blending amount. Therefore, the blending amount of the vanadium compound is preferably 0.001 to 10 parts by mass, more preferably 0.05 to 3 parts by mass based on 100 parts by mass of the total polymerizable monomers in the primer.

The hydroperoxide to be used in the composite resin of the present embodiment is not particularly limited and any known hydroperoxide may be used without limitation. Typical examples of the hydroperoxide include paramethanehydroperoxide, diisopropylbenzeneperoxide, 1,1,3,3-tetramethylbutylhydroperoxide, cumenehydroperoxide, t-hexylhydroperoxide, and t-butylhydroperoxide.

The hydroperoxide may be appropriately and selectively used in accordance with the blending amount and the structure of the radical-polymerizable monomer having no acidic group in the composite resin, or the radical-polymerizable monomer having an acidic group or a vanadium compound in the primer. However, from the viewpoint in permeation property in the primer, paramethanehydroperoxide, 1,1,3,3-tetramethylbutylhydroperoxide, t-hexylhydroperoxide, and t-butylhydroperoxide are preferable, and 1,1,3,3-tetramethylbutylhydroperoxide, t-hexylhydroperoxide, and t-butylhydroperoxide are more preferable. Further, of those, 1,1,3,3-tetramethylbutylhydroperoxide is most preferable because the volatility is relatively low.

It should be noted that, as required, those hydroperoxides may be used singly, or two or more of them may be used in combination.

The blending amount of the hydroperoxide is not particularly limited, and may be determined appropriately depending upon the kind and blending amount of the radical-polymerizable monomer having no acidic group in the composite resin, and the blending ratio of the other components. The blending amount of the hydroperoxide is preferably 0.01 to 20 parts by mass, more preferably 0.1 to 10 parts by mass, and most preferably 0.5 to 5 parts by mass based on 100 parts by mass of the radical-polymerizable monomer having no acidic group constituting the composite resin.

Further, a coloring material such as a pigment or a fluorescent pigment can be blended in the dental filling/restoration kit according to the present embodiment, in order to adjust the kit to the color tone of a tooth and a gum. Further, a UV-absorber may be added so as to prevent discoloring with respect to UV-light. Further, it is also preferred to blend a polymerization inhibitor so as to enhance the storage stability. Further, a stabilizer, a disinfectant, or the like may be added.

A method of using the primer of the dental filing/restoration kit according to the present embodiment is not particularly limited. In general, a method of applying a primer to a cavity using a brush, a spatula, a pen, a roller, or the like, or spraying the primer to the cavity can be adopted. Further, the primer may be applied a plurality of times. Further, in the case where it is necessary to use an etchant separately, the etchant may be used before applying the primer.

After the primer is applied or sprayed to the cavity, preferably, the primer is dried so as to evaporate excess water and solvent. Examples of the drying method include natural drying, heat drying, blast drying, drying under reduced pressure, and a combination thereof. However, considering drying the primer in the mouth, blast drying with the use of an air gun sending dried air is preferred.

Next, a composite resin is mounted on the dried primer to fill the cavity. At this time, the method of using the composite resin is not particularly limited. In general, the primer is mounted using a spatula or the like, and is arranged to the shape similar to the actual tooth. Finally, a filling/restoring portion is irradiated with visible light using a dental light irradiator, whereby the primer and composite resin in the filling/restoring portion can be cured.

Further, there is no particular limit to the package form of the dental filling/restoration kit according to the present embodiment. It is more preferred that each item of the kit is packaged in the same container as one paste of a composite resin and one liquid of a primer for convenience of easy operation.

EXAMPLES

Hereinafter, the present invention is described specifically by way of examples. The present invention is not limited to those examples. The description of the examples is made based on <<Example A>> listing examples according to the first embodiment and comparative examples and <<Example B>> listing mainly examples according to the second embodiment and comparative examples.

Example A

Tables 1 and 2 show the compositions of produced composite resins and the compositions of produced primers, respectively. Tables 3 and 4 show the compositions of the dental filling/restoration kits in the respective examples and comparative examples, and the results of an initial adhesion test at a filling portion and the results of an adhesion durability test at the filling portion, respectively.

First, the compounds used in the examples and comparative examples and the abbreviations thereof, the method of measuring an initial adhesion test between a tooth and a composite resin, the method of measuring an adhesion durability test of a composite resin with respect to a tooth, the method of producing a composite resin, and the method of producing a primer are described.

(1) Compound Used and Abbreviated Name Thereof
[Radical-Polymerizable Monomer Having Acidic Group]
"PM": a mixture in which 2-methacryloyloxyethyldihydrogen phosphate and bis(2-methacryloyloxyethyl)hydrogen phosphate are mixed at a mass ratio of 2:1
"MDP": 10-methacryloxydecyldihydrogen phosphate
"MAC-10": 11-methacryloyloxy-1,1-undecanedicarboxylic acid
[Radical-Polymerizable Monomer Having No Acidic Group]
"D-2.6E": 2,2'-bis(4-(methacryloxyethoxy)phenyl)propane
"BisGMA": 2,2'-bis[4-(2-hydroxy-3-methacryloxypropoxy)phenyl]propane
"3G": triethylene glycol dimethacrylate "UDMA": a mixture of 1,6-bis(methacrylethyloxycarbonylamino)2,2,4-trimethylhexane and 1,6-bis(methacrylethyloxycarbonylamino)2,4,4-trimethylhexane

[Water-Soluble Radical-Polymerizable Monomer Having No Acidic Group]
"HEMA": 2-hydroxyethyl methacrylate
"9G": polyethyleneglycol (polymerization degree: 9) dimethacrylate (structural formula represented by Chem 4)
"14G": polyethylene glycol (polymerization degree: 14) dimethacrylate (structural formula represented by Chem 5)
"BPE-1300": ethoxylated bisphenol A dimethacrylate (structural formula represented by Chem 6)
"M90G": methoxypolyethylene glycol methacrylate (structural formula represented by Chem 7)

Each of those is a radical-polymerizable monomer which may be mixed in an arbitrary ratio to water at 23° C.

[Polymerization Inhibitor]
"HQME": hydroquinone monomethyl ether
"BHT": 2,6-di-t-butyl-p-cresol

[Other Components]
"F1": a mixture obtained by mixing spherical silica-zirconia (average particle size: 0.4 μm) hydrophilized with γ-methacryloyloxypropyl trimethoxysilane with spherical silica-titania (average particle size: 0.08 μm) hydrophilized with γ-methacryloyloxypropyl trimethoxysilane in a mass ratio of 70:30
"F2": fumed silica (average particle size: 0.02 μm) surface-treated with methyltrichlorosilane
"MF": a substance obtained by crushing fluoroaluminosilicate glass powder (TOKUSO IONOMER, manufactured by Tokuyama Corporation) to a powder with an average particle size of 0.5 μm, using a wet-type continuous ball mill

[Chem 4]

[Chem 5]

[Chem 6]

[Chem 7]

n + m = 30

[Volatile Water-Soluble Organic Solvent]
"IPA": isopropyl alcohol.
Acetone

[Polymerization Initiator]
"CQ": camphorquinone
"DMBE": ethyl p-N,N-dimethylamino benzoate
"TPO": 2,4,6-trimethylbenzoyl diphenylphosphine oxide
"BTPO": bis(2,4,6-trimethylbenzoyl)phenylphosphine oxide
"PTSNa": sodium para-toluenesulfonate (NEW MY MILL, manufactured by Mitsui Mining Co., Ltd.), and thereafter, reforming the filler surface with 20 g of 5.0 N hydrochloric acid with respect to 1 g of the crushed powder for 20 minutes (2) Method of Measuring Initial Adhesive Strength of Composite Resin A cow was killed, and a foretooth of the cow was pulled within 24 hours after the killing. The pulled cow's foretooth was polished with emery paper of #600 under water injection, and the flat surface of an enamel and dentin was cut out so as to be parallel and flat to the labial surface. Next, the flat surface thus cut out was blown with compressed air for about 10 seconds to be dried. Then, a double-sided tape having a hole with a diameter of 3 mm was attached to the flat surface, and a paraffin wax having a hole with a thickness of 0.5 mm and a diameter of 8 mm was fixed with the center of the hole of the paraffin wax being aligned with the center of the hole of the double-sided tape attached previously, whereby a pseudo cavity was formed. A primer was applied to the pseudo cavity and left for 20 seconds. Then, the primer was blown with compressed air for about 10 seconds to be dried. Further, the resultant cavity was filled with a composite resin, followed by irradiation with visible light by a visible light irradiator (TOKUSO POWER LIGHT, manufactured by Tokuyama Corporation) for 30 seconds, whereby an adhesive test chip was produced.

The adhesive test chip was soaked in water at 37° C. for 24 hours, and thereafter, was stretched at a cross-head speed of 2 mm/min., using a tensile tester (AUTOGRAPH, manufactured by Shimadzu Corporation), whereby the tensile adhesion strength between the tooth and the composite resin was measured. The tensile adhesion strength between the tooth and the composite resin was measured respectively for 4 various test chips in each example or each comparative example. The average value of the four tensile adhesion strengths was used as the adhesive strength of the corresponding examples or comparative examples.

(3) Method of Testing Adhesion Durability

The adhesive test chip similar to that in the method of measuring initial adhesive strength was placed in a heat shock tester, soaked in a water tank at 4° C. for 1 minute, transferred to be soaked in a water tank at 60° C. for 1 minute, and returned to the water tank at 4° C. This operation was repeated 3,000 times. After that, the tensile adhesive strength was measured in the procedure similar to that of the measurement of initial adhesive strength. The tensile adhesive strength of four chips per test was measured by the method similar to the above, and the average value was used as the adhesive strength after the durability test, whereby the evaluation results of the adhesion durability were obtained.

(4) Preparation of Composite Resin

With respect to 6.0 g of BisGMA, 3.0 g of 3G, and 1.0 g of 9G, 0.05 g of BTPO, 0.01 g of HQME, and 0.003 g of BHT were added, and the mixture was stirred until it became uniform in a dark room to obtain a matrix. The obtained matrix and 16.3 g of F1 were mixed in an agate mortar, and deaerated under vacuum, whereby a light-curable composite resin CR1 with a filler filling ratio of 62% was obtained. Other composite resins (CR2 to CR16) were also produced in the compositions shown in Table 1 in the same procedure.

(5) Preparation of Primer 5.0 g of PM, 5.0 g of HEMA, 0.003 g of BHT, and 10.0 g of distilled water were stirred until they became uniform in a dark room to obtain a primer P1. Other primers (P2 to P13) were also produced in the compositions shown in Table 2 in the same procedure.

A dental filling/restoration kit in each example was obtained using a composite resin and a primer shown in Table 3, and an initial adhesion test and an adhesion durability test were conducted in each example. Table 3 shows the results.

TABLE 1

| | Composition of composite resin (part(s) by mass) | | | | |
|---|---|---|---|---|---|
| | Matrix composition | | | | |
| | Water-soluble polymerizable monomer having no acidic group | Other polymerizable monomers | Polymerization initiator | Others | Content of filler |
| CR1 | 9G(10) | BisGMA(60) + 3G(30) | BTPO(0.5) | HQME(0.1) + BHT(0.03) | F1(163) |
| CR2 | 14G(10) | BisGMA(60) + 3G(30) | BTPO(0.5) | HQME(0.1) + BHT(0.03) | F1(163) |
| CR3 | BPE-1300(10) | BisGMA(60) + 3G(30) | BTPO(0.5) | HQME(0.1) + BHT(0.03) | F1(163) |
| CR4 | HEMA(10) | BisGMA(60) + 3G(30) | BTPO(0.5) | HQME(0.1) + BHT(0.03) | F1(163) |
| CR5 | 90MG(10) | BisGMA(60) + 3G(30) | BTPO(0.5) | HQME(0.1) + BHT(0.03) | F1(163) |
| CR6 | 14G(10) | D-2.6E(60) + 3G(30) | BTPO(0.5) | HQME(0.1) + BHT(0.03) | F1(163) |
| CR7 | 14G(10) | D-2.6E(60) + UDMA(30) | BTPO(0.5) | HQME(0.1) + BHT(0.03) | F1(163) |
| CR8 | 14G(5) | BisGMA(60) + 3G(35) | BTPO(0.5) | HQME(0.1) + BHT(0.03) | F1(163) |
| CR9 | 14G(27) | BisGMA(60) + 3G(13) | BTPO(0.5) | HQME(0.1) + BHT(0.03) | F1(163) |
| CR10 | 14G(10) | BisGMA(60) + 3G(30) | CQ(0.5) + DMBE(0.5) | HQME(0.1) + BHT(0.03) | F1(163) |
| CR11 | 14G(10) | BisGMA(60) + 3G(30) | TPO(0.5) | HQME(0.1) + BHT(0.03) | F1(163) |
| CR12 | 14G(10) | BisGMA(60) + 3G(30) | BTPO(0.5) + DMBE(0.5) | HQME(0.1) + BHT(0.03) | F1(163) |
| CR13 | 14G(10) | BisGMA(60) + 3G(30) | BTPO(0.5) | HQME(0.1) + BHT(0.03) | F1(400) |
| CR14 | 14G(10) | BisGMA(60) + 3G(20) + PM(10) | BTPO(0.5) | HQME(0.1) + BHT(0.03) | F1(163) |
| CR15 | — | BisGMA(60) + 3G(40) | BTPO(0.5) | HQME(0.1) + BHT(0.03) | F1(163) |
| CR16 | — | BisGMA(60) + 3G(30) + PM(10) | BTPO(0.5) | HQME(0.1) + BHT(0.03) | F1(163) |

TABLE 2

Composition of primer (part(s) by mass)

| | Polymerizable monomer | | | | |
|---|---|---|---|---|---|
| | Having acidic group | Others | Water | Organic solvent | Others |
| P1 | PM(50) | HEMA(50) | Water(100) | — | BHT(0.03) |
| P2 | PM(100) | — | Water(20) | IPA(85) | BHT(0.03) |
| P3 | PM(50) | HEMA(50) | Water(20) | IPA(85) | BHT(0.03) |
| P4 | PM(50) | HEMA(50) | Water(20) | Acetone(85) | BHT(0.03) |
| P5 | MDP(50) | HEMA(50) | Water(20) | IPA(85) | BHT(0.03) |
| P6 | PM(30) + MAC-10(20) | HEMA(50) | Water(20) | IPA(85) | BHT(0.03) |
| P7 | MAC-10(50) | HEMA(50) | Water(20) | IPA(85) | BHT(0.03) |
| P8 | PM(40) | HEMA(50) + BisGMA(10) | Water(20) | IPA(85) | BHT(0.03) |
| P9 | PM(50) | HEMA(50) | Water(20) | IPA(85) | BHT(0.03) + MF(10) |
| P10 | PM(50) | HEMA(50) | Water(20) | IPA(85) | BHT(0.03) + BTPO(0.5) |
| P11 | PM(50) | HEMA(50) | Water(20) | IPA(85) | BHT(0.03) + MF(10) + F2(5) |
| P12 | PM(50) | HEMA(50) | Water(20) | IPA(85) | BHT(0.03) + MF(10) + F2(5) + BTPO(0.5) |
| P13 | PM(50) | HEMA(50) | Water(20) | IPA(85) | BHT(0.03) + BTPO(0.5) + PTSNa(1.0) |

TABLE 3

| | | | Adhesive strength/MPa (standard deviation) | | | |
|---|---|---|---|---|---|---|
| | Com- | | Initial | | After durability test | |
| Example No. | posite resin | Primer | Enamel | Dentin | Enamel | Dentin |
| 1 | CR1 | P1 | 18.2(3.2) | 11.3(2.8) | 15.2(1.2) | 9.8(2.5) |
| 2 | CR2 | P1 | 17.3(3.1) | 13.5(3.1) | 14.3(2.1) | 10.5(3.3) |
| 3 | CR3 | P1 | 18.1(4.1) | 12.2(4.1) | 15.0(3.1) | 10.0(3.2) |
| 4 | CR4 | P1 | 18.3(1.2) | 9.1(3.4) | 14.9(3.8) | 8.3(2.2) |
| 5 | CR5 | P1 | 18.2(3.5) | 9.3(1.3) | 15.1(3.3) | 8.6(2.3) |
| 6 | CR6 | P1 | 17.3(4.0) | 11.3(2.5) | 16.1(2.0) | 9.3(2.1) |
| 7 | CR7 | P1 | 18.1(5.3) | 13.1(1.9) | 14.8(1.1) | 10.3(2.5) |
| 8 | CR8 | P1 | 18.6(1.2) | 10.1(3.2) | 16.0(1.9) | 10.0(2.8) |
| 9 | CR9 | P1 | 17.5(4.1) | 12.2(1.8) | 15.0(4.2) | 9.3(2.8) |
| 10 | CR10 | P1 | 16.1(2.9) | 10.2(3.1) | 13.1(2.2) | 8.2(3.1) |
| 11 | CR11 | P1 | 17.1(3.8) | 11.5(2.0) | 15.6(3.8) | 9.9(1.0) |
| 12 | CR12 | P1 | 18.3(3.1) | 14.5(3.1) | 15.9(2.8) | 11.8(3.9) |
| 13 | CR13 | P1 | 17.2(3.3) | 11.6(3.2) | 15.2(1.9) | 9.6(3.0) |
| 14 | CR14 | P1 | 18.3(2.2) | 12.3(2.6) | 15.3(2.6) | 9.2(1.1) |
| 15 | CR2 | P2 | 18.0(5.2) | 11.3(2.1) | 16.0(3.4) | 10.9(2.8) |
| 16 | CR2 | P3 | 19.4(3.5) | 14.3(2.9) | 15.4(2.8) | 10.4(3.1) |
| 17 | CR2 | P4 | 19.2(3.1) | 14.5(3.2) | 16.7(4.3) | 12.1(1.4) |
| 18 | CR2 | P5 | 19.5(3.1) | 16.1(3.2) | 16.9(2.1) | 13.8(4.2) |
| 19 | CR2 | P6 | 17.3(4.1) | 14.8(3.0) | 15.3(2.9) | 12.0(2.8) |
| 20 | CR2 | P7 | 12.5(2.1) | 13.8(3.0) | 10.5(2.3) | 8.0(1.5) |
| 21 | CR2 | P8 | 18.5(3.2) | 12.4(2.1) | 15.3(2.1) | 9.2(1.2) |
| 22 | CR2 | P9 | 18.4(3.2) | 15.3(2.8) | 16.4(3.2) | 12.3(2.5) |
| 23 | CR2 | P10 | 18.3(2.1) | 18.9(2.1) | 14.2(2.1) | 13.1(2.5) |
| 24 | CR2 | P11 | 23.3(4.1) | 19.2(3.3) | 20.5(2.7) | 16.3(1.3) |
| 25 | CR2 | P12 | 23.0(1.3) | 18.9(1.3) | 20.0(1.8) | 16.9(2.2) |
| 26 | CR2 | P13 | 22.1(2.3) | 18.1(1.1) | 19.7(3.4) | 14.2(1.1) |

Measurements of Examples 1 to 26 were performed using a composite resin containing a water-soluble polymerizable monomer having no acidic group. Further, in Examples 1 to 14, the same primer was used, and in Examples 15 to 26, the kind of the primer was changed. In any of the results, high adhesive strength was obtained with respect to both the enamel and the dentin. Further, an adhesion durability test was conducted with respect to both the enamel and the dentin, and no considerable decrease in adhesion strength was seen.

Examples 1 to 5

Measurement was conducted using composite resins having different kinds of water-soluble polymerizable monomers having no acidic group. Compared with Example 4 using HEMA or Example 5 using MG, here, HEMA and 90MG were a monofunctional radical-polymerizable monomer as a water-soluble polymerizable monomer having no acidic group, the results of the initial adhesion test and the adhesion durability test tended to be more satisfactory in Examples 1 and 2 each using a polyfunctional radical-polymerizable monomer. In particular, an adhesion durability value with respect to a dentin was enhanced.

Examples 10 to 12

Measurement was conducted varying the kind of a polymerization initiator in the same blending ratio as that in Example 2. As a result, in Example 10 utilizing a composite resin using CQ that was an α-diketone-based polymerization initiator and DMBE, initial adhesive strength was slightly smaller and the durability of the adhesive strength was lower compared with those in the other examples.

Examples 22 and 24

Example 22 in which MF that was a polyvalent metal ion eluting filler was added to a primer and Example 24 in which surface-treated fumed silica and MF were added as inorganic fillers were produced. As a result, compared with Example 3 in which MF was not added, the initial adhesive strength with respect to a dentin was enhanced in Example 22. Further, in Example 22, the adhesion durability with respect to an enamel and a dentin was also enhanced. Further, Example 24 in which two kinds of inorganic particles were mixed exhibited more satisfactory initial adhesive strength and adhesion durability compared with those in Example 3.

Examples 17 to 20

Measurement was conducted varying the kind of a polymerizable monomer having an acidic group in a primer. As a result, Examples 17 and 18 in which the acidic group of the polymerizable monomer having an acidic group was a phosphate-based ester exhibited more satisfactory initial adhesive strength and adhesion durability, compared with those in Example 19 partially using MAC-10 in which the acidic group of the polymerizable monomer having an acidic group was a carboxyl group. Further, Example 20 using only MAC-10 as the polymerizable monomer having an acidic group had lower initial adhesive strength and adhesion durability compared with those in Examples 17 to 19.

Examples 23, 25, 26

Example 23 in which a polymerization initiator was contained in a primer, Example 25 in which a polymerization initiator and two kinds of inorganic fillers were added, and Example 26 using two kinds of polymerization initiators were produced. Any of those examples exhibited enhanced initial adhesive strength and adhesion durability compared with those in Example 3. Further, Example 25 in which both the inorganic filler and the polymerization initiator were added exhibited satisfactory initial adhesive strength and adhesion durability almost comparable to those of Example 24.

TABLE 4

| Comparative Example No. | Composite resin | Primer | Adhesive strength/MPa (standard deviation) | | | |
|---|---|---|---|---|---|---|
| | | | Initial | | After durability test | |
| | | | Enamel | Dentin | Enamel | Dentin |
| 1 | CR15 | P1 | 16.2(3.2) | 2.3(2.8) | 9.2(1.2) | 1.3(0.8) |
| 2 | CR15 | P3 | 17.2(3.2) | 2.3(2.2) | 9.7(2.2) | 1.0(2.2) |
| 3 | CR15 | P8 | 18.1(4.1) | 7.2(4.5) | 9.5(4.1) | 2.2(1.1) |
| 4 | CR15 | P9 | 24.1(3.3) | 18.6(1.1) | 17.3(4.1) | 7.4(3.1) |
| 5 | CR15 | P11 | 19.4(3.2) | 18.7(2.6) | 11.3(4.2) | 8.4(2.3) |
| 6 | CR16 | P1 | 17.2(2.5) | 3.3(1.3) | 10.3(2.5) | 2.1(2.1) |
| 7 | CR16 | P3 | 17.3(4.0) | 5.3(2.5) | 10.3(4.0) | 2.3(1.5) |
| 8 | CR16 | P8 | 18.1(5.3) | 7.1(2.9) | 10.1(3.2) | 2.1(1.9) |
| 9 | CR16 | P11 | 18.6(1.2) | 11.1(3.2) | 12.3(3.2) | 6.5(2.8) |

Comparative Examples 1 to 5

Each comparative example was produced in which the composition of a primer was varied using a composite resin containing no water-soluble polymerizable monomer having no acidic group. The adhesive strength was lower, and in particular, the adhesion durability was decreased considerably, compared with those in each example. Further, the adhesive strength with respect to a dentin was ⅕ or less of that in each example.

Comparative Examples 6 to 9

A composite resin containing no water-soluble polymerizable monomer having no acidic group and PM that was a polymerizable monomer having an acidic group was used to achieve such composition that both the composite resin and the primer contain a polymerizable monomer having an acidic group, a polymerizable monomer having no acidic group, and a polymerization initiator. Comparative Examples 6 to 9 were produced varying the composition of the primer.

Comparative Examples 6 to 9 exhibited higher adhesive strength compared with that in Comparative Examples 1 to 5. However, compared with that in each example, the adhesive strength was lower, in particular, the adhesive strength with respect to a dentin was ⅕ or less of that in each example, and the adhesion durability was decreased considerably.

Example B

Tables 6 and 7 show the compositions of the produced composite resins and Tables 8 and 9 show the compositions of the produced primers, respectively. Further, Tables 10, 11, and 12 show the compositions of the dental filling/restoration kits in the respective examples and comparative examples, and the results of an initial adhesion test of a filling portion and the results of an adhesion durability test, respectively.

First, the compounds used in the examples and comparative examples and the abbreviations thereof, the measurement method of an initial adhesion test between a tooth and a composite resin, the method of producing a composite resin, and the method of producing a primer are described.

(1) Compound Used and Abbreviation Thereof
[Radical-Polymerizable Monomer Having Acidic Group]
"PM": a mixture in which 2-methacryloyloxyethyldihydrogen phosphate and bis(2-methacryloyloxyethyl)hydrogen phosphate are mixed at a mass ratio of 2:1
"MDP": 10-methacryloxydecyldihydrogen phosphate
"MAC-10": 11-methacryloyloxy-1,1-undecanedicarboxylic acid
[Radical-Polymerizable Monomer Having No Acidic Group]
"D-2.6E": 2,2'-bis(4-(methacryloxyethoxy)phenyl)propane
"BisGMA": 2,2'-bis[4-(2-hydroxy-3-methacryloxypropoxy)phenyl]propane
"3G": triethylene glycol dimethacrylate
[Water-Soluble Radical-Polymerizable Monomer Having No Acidic Group]
"HEMA": 2-hydroxyethyl methacrylate
"14G": polyethylene glycol (polymerization degree: 14) dimethacrylate (structural formula represented by Chem 8)
"BPE-1300": ethoxylated bisphenol A dimethacrylate (structural formula represented by Chem 9)

[Chem 8]

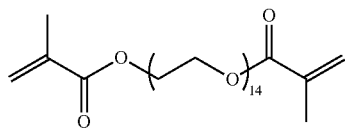

[Chem 9]

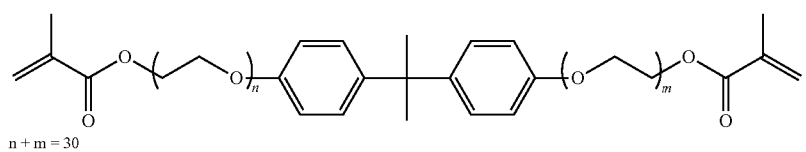

n + m = 30

[Volatile Water-Soluble Organic Solvent]
"IPA": isopropyl alcohol
Acetone
　[Tertiary Amine]
"DMBE": ethyl p-N,N-dimethylaminobenzoate
"TMPT": N,N-dimethyl p-toluidine
"DMEM": N,N-dimethylaminoethyl methacrylate
　[Photopolymerization Initiator]
"CQ": camphorquinone
"BN": benzil
"TPO": 2,4,6-trimethylbenzoyldiphenylphosphine oxide
"BTPO": bis(2,4,6-trimethylbenzoyl)phenylphosphine oxide
　[Polymerization Inhibitor]
"HQME": hydroquinone monomethyl ether
"BHT": 2,6-di-t-butyl-p-cresol
　[Basic Inorganic Compound]
"AO": alumina powder (average particle size: 0.02 μm)
"NaF": sodium fluoride (average particle size: 4.0 μm)
"CS": calcium silicate (average particle size: 5.0 μm)
"MF": a product obtained by crushing fluoroaluminosilicate glass powder (TOKUSO IONOMER, manufactured by Tokuyama Corporation) to an average particle size of 0.5 μm, using a wet-type continuous ball mill (NEW MY MILL, manufactured by Mitsui Mining Co., Ltd.), and thereafter, modifying the filler surface with 20 g of 5.0 N hydrochloric acid with respect to 1 g of the crushed powder for 20 minutes.
"MF-2": fluoroaluminosilicate glass powder (TOKUSO IONOMER, manufactured by Tokuyama Corporation, average particle size: 4.0 μm, 24-hour elution ion amount: 31 meq/g filler) used as it is.
　[Hydroperoxide]
"Perocta H": 1,1,3,3-tetramethylbutyl hydroperoxide (compound represented by Chem 10)
"Permenta H": paramenthane hydroperoxide (compound represented by Chem 11)
"Perbutyl H": t-butyl hydroperoxide (compound represented by Chem 12)

[Chem 10]

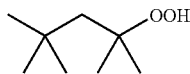

[Chem 11]

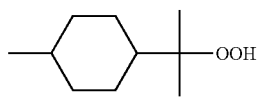

[Chem 12]

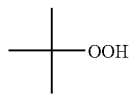

[Vanadium Compound]
"BMOV": bis(maltolato)oxovanadium (IV)
"VO(OPr)3": vanadium (V) oxytriisopropoxide
　[Photoacid Generator]
"IMDPI": (compound represented by Chem 13)
"TAZ": (compound represented by Chem 14)

[Chem 13]

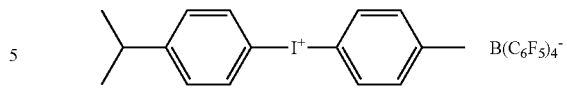

[Chem 14]

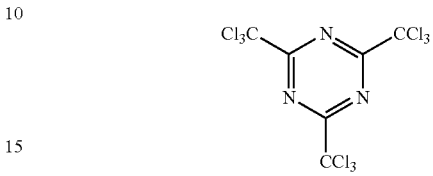

[Other Components]
"F1": a mixture obtained by mixing spherical silica-zirconia (average particle size: 0.4 μm) hydrophobized with γ-methacryloyloxypropyl trimethoxysilane with spherical silica-titania (average particle size: 0.08 μm) hydrophobized with γ-methacryloyloxypropyl trimethoxysilane in a mass ratio of 70:30.
"F2": fumed silica (average particle size: 0.02 μm) surface-treated with methyltrichlorosilane.

(2) Method of Measuring Adhesive Strength of Composite Resin with Thickness of 0.5 mm A cow was killed, and a foretooth of the cow was extracted within 24 hours after the killing. The extracted cow's foretooth was polished with emery paper of #600 under water injection, and enamel and dentin flat surfaces were cut out so as to be parallel to the labial surface and flat. Next, the flat surfaces thus cut out were sprayed with compressed air for about 10 seconds and dried. Then, a double-sided tape having a hole with a diameter of 3 mm was attached to each of the flat surfaces, and paraffin wax having a hole with a thickness of 0.5 mm and a diameter of 8 mm was fixed with the center of the hole of the paraffin wax being aligned with the center of the hole of the double-sided tape attached previously, whereby a pseudo cavity was formed. A primer was applied to the pseudo cavity and left to stand for 20 seconds. Then, the primer was sprayed with compressed air for about 10 seconds to be dried. Further, the resultant cavity was filled with a composite resin, and irradiated with visible light by a visible light irradiator (TOKUSO POWER LIGHT, manufactured by Tokuyama Corporation) for 30 seconds, whereby an adhesive test chip in which the thickness of the composite resin was 0.5 mm was produced.

The adhesive test chip was soaked in water at 37° C. for 24 hours, and thereafter, was stretched at a cross-head speed of 2 mm/min, using a tensile tester (AUTOGRAPH, manufactured by Shimadzu Corporation), whereby the tensile adhesion strength between the tooth and the composite resin was measured. The tensile adhesion strength between the tooth and the composite resin was measured respectively for four test chips of various kinds in each example or each comparative example. The average value of four measurements for the tensile adhesion strength was used as the adhesive strength of the corresponding example or comparative example.

(3) Method of Measuring Adhesive Strength of Composite Resin with Thickness of 1.5 mm An adhesive test chip in which the thickness of a composite resin was 1.5 mm was produced using paraffin wax having a hole with a thickness of 1.5 mm and a diameter of 8 mm, in place of the paraffin wax having a hole with a thickness of 0.5 mm and a diameter of 8 mm by the same method as the method of measuring adhesive strength of a composite resin with a thickness of 0.5 mm. Then, the adhesive strength was measured by the same method as the method of measuring adhesive strength of a composite resin with a thickness of 0.5 mm.

(4) Method of Measuring Adhesive Strength of Composite Resin with Thickness of 2.5 mm An adhesive test chip in which the thickness of a composite resin was 2.5 mm was produced using paraffin wax having a hole with a thickness of 2.5 mm and a diameter of 8 mm, in place of the paraffin wax having a hole with a thickness of 0.5 mm and a diameter of 8 mm by the same method as the method of measuring adhesive strength of a composite resin with a thickness of 0.5 mm. Then, the adhesive strength was measured by the same method as the method of measuring adhesive strength of a composite resin with a thickness of 0.5 mm.

(5) Measurement of Basicity of Inorganic Compound

Phosphoric acid was added to a mixture in which distilled water and ethanol were mixed in a volume ratio of 1:1, and the pH of the mixture was adjusted to 2.50 by the measurement with a pH meter (main body: Ion meter IM20E, electrode: GST-5721S, both of which are manufactured by DKK-TOA Corporation) at 23° C., whereby a dispersion medium for measurement was obtained. One gram of a basic inorganic compound was added to 20 g of the dispersion, and the whole was stirred with a stirrer at 23° C. for 2 minutes. Immediately after the stirring, the mixture was measured with a pH meter similarly. The value obtained by subtracting the pH value of the dispersion medium itself from the pH value of the dispersion was used as a pH difference. Table 5 shows measurement values and pH differences in various inorganic basic compounds.

(6) Method of Measuring Eluted Ions 0.2 g of the dispersion was weighed in a 100-ml sample tube, and diluted to 1% by mass using IPA. The solution thus obtained was filtered with a syringe filter, and the presence or absence of the elution of metal ions was checked by subjecting the filtrate to an inductively coupled plasma (ICP) emission spectral analysis.

TABLE 5

|  | Dispersion pH | pH differnece | Eluted metal ions |
|---|---|---|---|
| AO | 2.58 | 0.08 | None |
| FNa | 5.36 | 2.86 | $Na^+$ |
| CS | 8.08 | 5.58 | $Ca^{2+}$ |
| MF | 2.68 | 0.18 | $Al^{3+}$, $La^{3+}$ |
| MF | 2.71 | 0.21 | $Al^{3+}$, $La^{3+}$ |

(7) Preparation of Composite Resin

With respect to 6.0 g of BisGMA, 3.0 g of 3G, and 1.0 g of 14G, 0.05 g of BTPO, 0.05 g of DMBE, 0.01 g of HQME, and 0.003 g of BHT were added, and the mixture was stirred until it became uniform in a dark room to obtain a matrix. The obtained matrix was mixed with 15.5 g of F1 and 8.0 g of AO in an agate mortar, and deaerated under vacuum, whereby a light-curable composite resin CR1 with a filler filling ratio of 61.7% was obtained. Other composite resins (CR2 to CR40) were produced in the compositions shown in Tables 6 and 7 in the same procedure

TABLE 6

| | Composition of composite resin (parts by mass) | | | | | |
|---|---|---|---|---|---|---|
| | Matrix composition | | | | Basic inorganic | |
| | Polymerizable monomer | Tertiary amine | Photopolymerization initiator | Others | material (content) | Filler (content) |
| CR1 | BisGMA(60) + 3G(30) + 14G(10) | DMBE(0.5) | BTPO(0.5) | HQME(0.1) + BHT(0.03) | AO(8) | F1(155) |
| CR2 | BisGMA(60) + 3G(30) + 14G(10) | DMBE(0.5) | BTPO(0.5) | HQME(0.1) + BHT(0.03) | NaF(8) | F1(155) |
| CR3 | BisGMA(60) + 3G(30) + 14G(10) | DMBE(0.5) | BTPO(0.5) | HQME(0.1) + BHT(0.03) | CS(8) | F1(155) |
| CR4 | BisGMA(60) + 3G(30) + 14G(10) | DMBE(0.5) | BTPO(0.5) | HQME(0.1) + BHT(0.03) | MF(8) | F1(155) |
| CR4-2 | BisGMA(60) + 3G(30) + 14G(10) | DMBE(0.5) | BTPO(0.5) | HQME(0.1) + BHT(0.03) | MF-2(8) | F1(155) |
| CR5 | BisGMA(60) + 3G(30) + 14G(10) | DMBE(0.5) | BTPO(0.5) | HQME(0.1) + BHT(0.03) | MF(30) | F1(133) |
| CR6 | BisGMA(60) + 3G(30) + 14G(10) | DMBE(0.5) | BTPO(0.5) | HQME(0.1) + BHT(0.03) | MF(80) | F1(83) |
| CR7 | BisGMA(60) + 3G(30) + 14G(10) | DMBE(0.5) | TPO(0.5) | HQME(0.1) + BHT(0.03) | MF(8) | F1(155) |
| CR8 | BisGMA(60) + 3G(30) + 14G(10) | DMBE(0.5) | CQ(0.5) | HQME(0.1) + BHT(0.03) | MF(8) | F1(155) |
| CR9 | BisGMA(60) + 3G(30) + 14G(10) | DMBE(0.5) | BN(0.5) | HQME(0.1) + BHT(0.03) | MF(8) | F1(155) |
| CR10 | BisGMA(60) + 3G(30) + 14G(10) | DBME(2.0) | BTPO(0.5) | HQME(0.1) + BHT(0.03) | FASG(8) | F1(155) |
| CR11 | BisGMA(60) + 3G(30) + 14G(10) | TMPT(0.5) | BTPO(0.5) | HQME(0.1) + BHT(0.03) | MF(8) | F1(155) |
| CR12 | BisGMA(60) + 3G(30) + 14G(10) | DMEM(0.5) | BTPO(0.5) | HQME(0.1) + BHT(0.03) | MF(8) | F1(155) |
| CR13 | BisGMA(60) + 3G(30) + BPE-1300(10) | DMBE(0.5) | BTPO(0.5) | HQME(0.1) + BHT(0.03) | MF(8) | F1(155) |
| CR14 | BisGMA(60) + 3G(30) + HEMA(10) | DMBE(0.5) | BTPO(0.5) | HQME(0.1) + BHT(0.03) | MF(8) | F1(155) |
| CR15 | BisGMA(60) + 3G(40) | DMBE(0.5) | BTPO(0.5) | HQME(0.1) + BHT(0.03) | MF(8) | F1(155) |
| CR16 | BisGMA(60) + 3G(35) + 14G(5) | DMBE(0.5) | BTPO(0.5) | HQME(0.1) + BHT(0.03) | MF(8) | F1(155) |
| CR17 | BisGMA(60) + 3G(13) + 14G(27) | DMBE(0.5) | BTPO(0.5) | HQME(0.1) + BHT(0.03) | MF(8) | F1(155) |
| CR18 | BisGMA(60) + 3G(30) + 14G(10) | DMBE(0.5) | BTPO(0.5) | HQME(0.1) + BHT(0.03) | MF(8) | Fl(392) |
| CR19 | BisGMA(60) + 3G(30) + 14G(10) | | BTPO(0.5) | HQME(0.1) + BHT(0.03) | | Fl(163) |
| CR20 | BisGMA(60) + 3G(30) + 14G(10) | DMBE(0.5) | BTPO(0.5) | HQME(0.1) + BHT(0.03) | | Fl(163) |
| CR21 | BisGMA(60) + 3G(30) + 14G(10) | | BTPO(0.5) | HQME(0.1) + BHT(0.03) | MF(8) | F1(155) |
| CR22 | BisGMA(60) + 3G(30) + PM(10) | DMBE(0.5) | BTPO(0.5) | HQME(0.1) + BHT(0.03) | MF(8) | F1(155) |

TABLE 7

Composition of composite resin (parts by mass)

| | Matrix composition | | | | | Basic inorganic material (content) | Filler (content) |
|---|---|---|---|---|---|---|---|
| | Polymerizable monomer | Tertiary amine | Photopolymerization initiator | Hydroperoxide | Others | | |
| CR23 | BisGMA(60) + 3G(30) + 14G(10) | DMBE(0.5) | BTPO(0.5) | Perocta H (1.0) | HQME(0.1) + BHT(0.03) | AO(8) | F1(155) |
| CR24 | BisGMA(60) + 3G(30) + 14G(10) | DMBE(0.5) | BTPO(0.5) | Perocta H (1.0) | HQME(0.1) + BHT(0.03) | FNa(8) | F1(155) |
| CR25 | BisGMA(60) + 3G(30) + 14G(10) | DMBE(0.5) | BTPO(0.5) | Perocta H (1.0) | HQME(0.1) + BHT(0.03) | CS(8) | F1(155) |
| CR26 | BisGMA(60) + 3G(30) + 14G(10) | DMBE(0.5) | BTPO(0.5) | Perocta H (1.0) | HQME(0.1) + BHT(0.03) | MF(8) | F1(155) |
| CR27 | BisGMA(60) + 3G(30) + 14G(10) | DMBE(1.0) | BTPO(0.5) | Perocta H (1.0) | HQME(0.1) + BHT(0.03) | MF(8) | F1(155) |
| CR28 | BisGMA(60) + 3G(30) + 14G(10) | DMBE(1.0) | BTPO(0.5) | Perocta H (0.5) | HQME(0.1) + BHT(0.03) | MF(8) | F1(155) |
| CR29 | BisGMA(60) + 3G(30) + 14G(10) | DMBE(1.0) | BTPO(0.5) | Perocta H (2.0) | HQME(0.1) + BHT(0.03) | MF(8) | F1(155) |
| CR30 | BisGMA(60) + 3G(30) + 14G(10) | DMBE(1.0) | BTPO(0.5) | Permenta H (1.0) | HQME(0.1) + BHT(0.03) | MF(8) | F1(155) |
| CR31 | BisGMA(60) + 3G(30) + 14G(10) | DMBE(1.0) | BTPO(0.5) | Perbutyl H (1.0) | HQME(0.1) + BHT(0.03) | MF(8) | F1(155) |
| CR32 | BisGMA(60) + 3G(30) + 14G(10) | DMBE(1.0) | CQ(0.5) | Perocta H (1.0) | HQME(0.1) + BHT(0.03) | MF(8) | F1(155) |
| CR33 | BisGMA(60) + 3G(30) + 14G(10) | DBME(1.0) | BN(0.5) | Perocta H (1.0) | HQME(0.1) + BHT(0.03) | MF(8) | F1(155) |
| CR34 | D-2.6E(40) + BisGMA(35) + 3G(15) + 14G(10) | DBME(1.0) | BTPO(0.5) | Perocta H (1.0) | HQME(0.1) + BHT(0.03) | MF(8) | F1(155) |
| CR35 | D-2.6E(40) + BisGMA(35) + 3G(15) + 14G(10) | DBME(1.0) | CQ(0.5) IMDPI(1.0) | Perocta H (1.0) | HQME(0.1) + BHT(0.03) | MF(8) | F1(155) |
| CR36 | D-2.6E(40) + BisGMA(35) + 3G(15) + 14G(10) | DBME(1.0) | CQ(0.5) TAZ(0.5) | Perocta H (1.0) | HQME(0.1) + BHT(0.03) | MF(8) | F1(155) |
| CR37 | D-2.6E(40) + BisGMA(35) + 3G(15) + 14G(10) | DBME(1.0) | BTPO(0.5) | Perocta H (1.0) | HQME(0.1) + BHT(0.03) | MF(8) | F1(392) |
| CR38 | BisGMA(60) + 3G(30) + 14G(10) | | BTPO(0.5) | Perocta H (1.0) | HQME(0.1) + BHT(0.03) | | F1(163) |
| CR39 | BisGMA(60) + 3G(30) + 14G(10) | DMBE(1.0) | BTPO(0.5) | Perocta H (1.0) | HQME(0.1) + BHT(0.03) | | F1(163) |
| CR40 | BisGMA(60) + 3G(30) + 14G(10) | | BTPO(0.5) | Perocta H (1.0) | HQME(0.1) + BHT(0.03) | MF(8) | F1(155) |

(8) Preparation of a Primer 5.0 g of PM, 5.0 g of HEMA, 0.003 g of BHT, and 10.0 g of distilled water were stirred until they became uniform in a dark room to obtain a primer P1. Other primers (P2 to P18) were produced in the compositions shown in Tables 8 and 9 in the same procedure.

TABLE 8

Composition of primer (parts by mass)

| | Polymerizable monomer | | Water | Organic solvent | Others |
|---|---|---|---|---|---|
| | Having an acidic group | Others | | | |
| P1 | PM(50) | HEMA(50) | Water(100) | — | BHT(0.03) |
| P2 | PM(100) | — | Water(20) | IPA(85) | BHT(0.03) |
| P3 | PM(50) | HEMA(50) | Water(20) | IPA(85) | BHT(0.03) |
| P4 | MPD(50) | HEMA(50) | Water(20) | IPA(85) | BHT(0.03) |
| P5 | MAC-10(50) | HEMA(50) | Water(20) | IPA(85) | BHT(0.03) |
| P6 | PM(40) | HEMA(50) + BisGMA(10) | Water(20) | IPA(85) | BHT(0.03) |
| P7 | PM(50) | HEMA(50) | Water(20) | IPA(85) | BHT(0.03) + MF(10) |
| P8 | PM(50) | HEMA(50) | Water(20) | IPA(85) | BHT(0.03) + MF(10) + F2(5) |
| P9 | PM(50) | HEMA(50) | Water(20) | IPA(85) | BHT(0.03) + MF(10) + F2(5) + BTPO(0.5) |
| P10 | PM(50) | HEMA(50) | Water(20) | IPA(85) | BHT(0.03) + MF(10) + F2(5) + BTPO(0.5) + DMBE(0.5) |

TABLE 9

| | Composition of primer (parts by mass) | | | | | |
|---|---|---|---|---|---|---|
| | Polymerizable monomer | | | | | |
| | Having an acidic group | Others | Water | Vanadium compound | Organic solvent | Others |
| P11 | PM(50) | HEMA(50) | Water(20) | BMOV(0.2) | IPA(150) | BHT(0.03) |
| P12 | PM(50) | HEMA(50) | Water(20) | BMOV(0.5) | IPA(150) | BHT(0.03) |
| P12-2 | PM(50) | HEMA(50) | Water(20) | BMOV(1.0) | IPA(150) | BHT(0.03) |
| P13 | PM(50) | HEMA(50) | Water(20) | VO(OPr)3(0.5) | IPA(150) | BHT(0.03) |
| P14 | PM(45) | HEMA(45) + 3G(4) + BisGMA(6) | Water(20) | BMOV(0.5) | IPA(150) | BHT(0.03) |
| P15 | PM(45) | HEMA(45) + 3G(4) + BisGMA(6) | Water(20) | BMOV(0.5) | IPA(150) | BHT(0.03) + MF(10) |
| P16 | PM(45) | HEMA(45) + 3G(4) + BisGMA(6) | Water(20) | BMOV(0.5) | IPA(150) | BHT(0.03) + MF(10) + F2(10) |
| P16-2 | PM(45) | HEMA(45) + 3G(4) + BisGMA(6) | Water(20) | BMOV(1.0) | IPA(150) | BHT(0.03) + MF(10) + F2(10) |
| P17 | PM(45) | HEMA(45) + 3G(4) + BisGMA(6) | Water(20) | BMOV(0.5) | IPA(150) | BHT(0.03) + MF(10) + F2(10) + BTPO(0.5) |
| P18 | PM(45) | HEMA(45) + 3G(4) + BisGMA(6) | Water(20) | BMOV(0.5) | Acetone(150) | BHT(0.03) + MF(10) + F2(10) + BTPO(0.5) |

A dental filling/restoration kit in each example was obtained using a composite resin and a primer shown in Tables 10, 11, and 12, and an adhesion test was conducted in each example and each comparative example. Tables 10, 11, and 12 show the results.

TABLE 10

| | Composite resin | Primer | Adhesive strength/MPa (standard deviation) | | | |
|---|---|---|---|---|---|---|
| | | | 0.5 mm | | 1.5 mm | |
| | | | Enamel | Dentin | Enamel | Dentin |
| Example No. | | | | | | |
| 1 | CR1 | P1 | 17.6(2.3) | 12.2(3.1) | 12.5(3.2) | 7.2(3.1) |
| 2 | CR2 | P1 | 17.2(3.1) | 12.5(2.8) | 12.8(2.4) | 8.2(2.2) |
| 3 | CR3 | P1 | 17.8(3.3) | 13.0(1.1) | 12.2(2.1) | 9.9(2.8) |
| 4 | CR4 | P1 | 18.1(3.2) | 13.9(2.1) | 14.0(3.5) | 10.5(2.1) |
| 4-2 | CR4-2 | P1 | 18.0(3.6) | 14.0(2.8) | 13.9(1.3) | 11.0(2.7) |
| 5 | CR5 | P1 | 18.2(3.3) | 14.0(3.2) | 14.1(2.5) | 11.9(2.3) |
| 6 | CR6 | P1 | 17.7(1.7) | 13.1(2.1) | 13.2(3.3) | 9.8(2.7) |
| 7 | CR7 | P1 | 18.0(3.3) | 13.2(2.1) | 13.8(2.1) | 9.8(2.5) |
| 8 | CR8 | P1 | 17.1(1.8) | 12.5(1.4) | 12.7(2.2) | 8.0(2.6) |
| 9 | CR9 | PI | 17.2(4.3) | 12.2(2.1) | 11.8(1.1) | 7.9(1.7) |
| 10 | CR10 | P1 | 18.1(3.2) | 14.2(2.4) | 14.4(3.1) | 11.7(3.1) |
| 11 | CR11 | P1 | 18.2(3.1) | 13.8(3.2) | 13.3(1.2) | 9.2(2.0) |
| 12 | CR12 | P1 | 17.2(1.2) | 13.2(1.2) | 11.0(2.3) | 7.5(2.1) |
| 13 | CR13 | P1 | 18.0(4.0) | 13.3(2.8) | 13.9(2.6) | 10.3(2.0) |
| 14 | CR14 | P1 | 17.8(1.9) | 13.2(1.5) | 13.1(4.2) | 9.4(3.1) |
| 16 | CR16 | P1 | 17.6(2.1) | 12.8(1.1) | 12.2(2.0) | 7.2(3.1) |
| 17 | CR17 | P1 | 17.9(1.2) | 13.3(2.6) | 13.7(1.7) | 10.0(2.8) |
| 18 | CR18 | P1 | 18.5(2.9) | 14.2(1.1) | 14.2(2.8) | 10.8(2.5) |
| 19 | CR4 | P2 | 18.5(3.4) | 12.7(2.1) | 14.1(2.5) | 9.2(3.1) |
| 20 | CR4 | P3 | 18.9(1.2) | 14.2(2.8) | 14.7(3.1) | 12.0(1.1) |
| 21 | CR4 | P4 | 18.1(2.5) | 14.9(2.5) | 14.9(2.7) | 11.8(2.3) |
| 22 | CR4 | P5 | 11.6(2.9) | 13.2(1.1) | 10.5(1.2) | 12.1(3.2) |
| 23 | CR4 | P6 | 19.2(3.2) | 15.8(2.1) | 15.5(3.3) | 12.6(2.1) |
| 24 | CR4 | P7 | 19.2(2.7) | 15.3(2.5) | 15.8(1.8) | 13.6(1.8) |
| 25 | CR4 | P8 | 21.1(3.2) | 18.1(2.1) | 20.1(2.9) | 15.2(2.4) |
| 26 | CR4 | P9 | 21.3(3.2) | 18.6(2.5) | 21.5(3.7) | 16.2(1.6) |
| 27 | CR4 | P10 | 22.1(3.5) | 19.8(3.4) | 21.7(2.4) | 18.3(4.0) |
| Comparative Example No. | | | | | | |
| 15 | CR15 | P1 | 16.3(3.1) | 9.2(1.1) | — | — |

TABLE 11

| Example No. | Composite resin | Primer | Adhesive strength/Mpa (standard deviation) 2.5 mm Enamel | Dentin |
|---|---|---|---|---|
| 28 | CR4 | P3 | 6.1(4.1) | 4.3(2.1) |
| 29 | CR23 | P11 | 12.3(3.1) | 6.2(3.1) |
| 30 | CR24 | P11 | 13.7(2.8) | 7.8(1.3) |
| 31 | CR25 | P11 | 16.3(2.1) | 8.4(2.1) |
| 32 | CR26 | P11 | 17.2(1.8) | 9.2(1.9) |
| 33 | CR27 | P11 | 17.8(3.2) | 10.5(2.2) |
| 34 | CR28 | P11 | 17.3(1.8) | 9.3(2.1) |
| 35 | CR29 | P11 | 18.0(3.3) | 12.1(2.5) |
| 36 | CR30 | P11 | 17.1(1.5) | 9.7(2.7) |
| 37 | CR31 | P11 | 17.3(4.3) | 11.0(3.1) |
| 38 | CR32 | P11 | 16.9(2.2) | 9.1(2.2) |
| 39 | CR33 | P11 | 16.8(4.2) | 8.8(1.8) |
| 40 | CR34 | P11 | 18.9(2.9) | 13.4(2.5) |
| 41 | CR35 | P11 | 18.0(3.1) | 12.2(2.3) |
| 42 | CR36 | P11 | 17.9(1.3) | 12.4(2.5) |
| 43 | CR37 | P11 | 17.2(1.2) | 11.0(2.3) |
| 44 | CR27 | P12 | 18.0(1.4) | 11.3(1.9) |
| 44-2 | CR27 | P12-2 | 18.5(2.1) | 12.3(1.7) |
| 45 | CR27 | P13 | 18.2(2.3) | 11.5(2.5) |
| 46 | CR27 | P14 | 18.2(1.9) | 13.1(3.2) |
| 47 | CR27 | P15 | 19.3(3.2) | 15.4(1.8) |
| 48 | CR27 | P16 | 20.4(2.8) | 16.7(3.4) |
| 48-2 | CR27 | P16-2 | 20.2(1.9) | 17.9(2.2) |
| 49 | CR27 | P17 | 20.3(2.9) | 17.5(2.3) |
| 50 | CR27 | P18 | 20.4(3.2) | 17.6(2.8) |

TABLE 12

| | Composite resin | Primer | Adhesive strength/MPa (standard deviation) | | | | | |
|---|---|---|---|---|---|---|---|---|
| | | | 0.5 mm | | 1.5 mm | | 2.5 mm | |
| | | | Enamel | Dentin | Enamel | Dentin | Enamel | Dentin |
| Example 51 | CR19 | P1 | 17.3(3.1) | 13.5(3.1) | 5.2(1.2) | 1.3(0.8) | | |
| Example 52 | CR19 | P10 | 23.1(3.2) | 19.3(2.8) | 10.2(3.5) | 3.2(1.8) | | |
| Example 53 | CR20 | P1 | 18.3(3.1) | 14.5(3.1) | 6.3(2.2) | 2.1(1.2) | | |
| Example 54 | CR20 | P10 | 21.8(3.7) | 19.1(3.2) | 9.8(2.3) | 2.9(1.2) | | |
| Example 55 | CR21 | P10 | 22.8(4.2) | 19.1(2.3) | 12.2(3.1) | 5.7(1.1) | | |
| Comparative Example 6 | CR22 | P1 | 16.3(2.8) | 11.5(4.2) | 2.5(1.9) | 1.2(0.6) | | |
| Example 56 | CR38 | P11 | | | | | 11.2(3.5) | 2.1(0.2) |
| Example 57 | CR38 | P17 | | | | | 16.2(3.1) | 6.2(3.1) |
| Example 58 | CR39 | P11 | | | | | 11.7(3.3) | 3.2(0.4) |
| Example 59 | CR39 | P17 | | | | | 17.2(3.2) | 9.5(3.3) |
| Example 60 | CR40 | P11 | | | | | 10.7(1.3) | 3.0(0.4) |

Measurement of Examples 1 to 50 was conducted using a composite resin containing a polymerizable monomer having no acidic group, a tertiary amine compound, and a basic inorganic material. Further, the measurement was conducted using the same primer in Examples 1 to 18 and varying the kind of a primer in Examples 19 to 28. In any of the results, satisfactory adhesive strength was exhibited even in the case where the thickness of the composite resin was large (1.5 mm) with respect to both an enamel and a dentin. Further, the measurement was conducted using the same primer in Examples 29 to 43 and varying the kind of a primer in Examples 44 to 50. In any of the results, satisfactory adhesive strength was exhibited in the case where the thickness of the composite resin was 2.5 mm with respect to both an enamel and a dentin.

Examples 1 to 6

The measurement was conducted using composite resins in which the kind and content of the basic inorganic material were different. By filling the primer layer applied to a tooth with a composite resin containing a tertiary amine compound and a basic inorganic material, a neutralization reaction is effected between the basic inorganic material with a relatively high basicity and the acidic group of PM that is the radical-polymerizable monomer having an acidic group at a contact interface between the primer layer and the composite resin, and the acidity of the acidic group is weakened, whereby the effect of promoting the polymerization of the tertiary amine compound can be enhanced. Therefore, the polymerization of the composite resin that is in contact with the primer layer as well as the primer layer is likely to be completed. Consequently, even in the case of using any basic inorganic material, stable adhesive strength was exhibited in both the cases where the thickness of the composite resin was 0.5 mm and 1.5 mm.

Examples 7 to 12

The measurement was conducted using composite resins in which the kinds of the tertiary amine compound and the photopolymerization initiator were different. Even in the case of using any of the tertiary amine compounds and the photopolymerization initiators, stable adhesive strength was exhibited in both the cases where the thickness of the composite resin was 0.5 mm and 1.5 mm. However, in Examples 8 and 9, the adhesive strength was decreased slightly compared with those in the other examples, since CQ and BN that were α-diketone-based photopolymerization initiators were used respectively.

Examples 13 and 14

Examples 13 and 14, in which the kind of the water-soluble radical-polymerizable monomer having no acidic group was varied in the same composition ratio as that in Example 1, were evaluated. Compared with Example 14 using HEMA that was a monofunctional radical-polymerizable monomer as the water-soluble radical-polymerizable monomer having no acidic group, the adhesive strength was more satisfactory in Example 13 using a polyfunctional radical-polymerizable monomer, irrespective of the thickness of the composite resin. Particularly, in the case where the thickness of the composite resin was 1.5 mm, the adhesive strength with respect to a dentin in Example 13 was higher than that in Example 14.

Comparative Example 15 and Examples 16 and 17

Comparative Example 15 and Examples 16 and 17, in which the content ratio of the water-soluble radical-polymerizable monomer having no acidic group was varied in the composition of Example 1, were evaluated. Compared with Comparative Example 15 containing no the water-soluble radical-polymerizable monomer having no acidic group, the adhesive strength was more satisfactory in Examples 16 and 17 containing the water-soluble radical-polymerizable monomer having no acidic group, irrespective of the thickness of the composite resin.

Example 18

Example 18 was evaluated, in which the content ratio of a filler was varied in the composition of Example 4. Satisfactory adhesive strength was exhibited irrespective of the thickness of the composite resin.

Examples 24 and 25

Example 24 in which MF that was a polyvalent metal ion eluting filler was added to a primer and Example 25 in which fumed silica subjected to surface treatment and MF were added as an inorganic filler were evaluated. As a result, in a test chip in which the thickness of a composite resin was 0.5 mm, compared with Example 20 with no MF added, the adhesive strength with respect to a dentin was enhanced in Example 24. Further, the adhesion durability with respect to an enamel and a dentin was also enhanced in Example 25. Further, in a test chip in which the thickness of the composite resin was 1.5 mm, compared with Example 20, the adhesive strength with respect to an enamel and a dentin was enhanced in both Examples 24 and 25.

Examples 21 to 23

The evaluation was conducted varying the kind of the radical-polymerizable monomer having an acidic group and the content of the radical-polymerizable monomer having no acidic group in the primer. As a result, Example 21 in which the acidic group of the radical-polymerizable monomer having an acidic group was a phosphate-based ester exhibited more satisfactory adhesive strength with respect to an enamel irrespective of the thickness of the composite resin, compared with Example 22 using MAC-10 in which the acidic group of the radical-polymerizable monomer having an acidic group was a carboxyl group. Further, Example 23 containing the radical-polymerizable monomer having no acidic group exhibited higher adhesive strength irrespective of the thickness of the composite resin, compared with Examples 21 and 22.

Example 26

Example 26 in which the photopolymerization initiator and two kinds of fillers were added to the primer was evaluated. Compared with Example 20, Example 26 in which both the filler and the polymerization initiator were added exhibited satisfactory adhesive strength almost comparable to that in Example 25 described above irrespective of the thickness of the composite resin.

Example 27

Example 27 in which the aromatic tertiary amine compound was contained in the primer was evaluated. Example 27 exhibited enhanced adhesive strength with respect to an enamel and a dentin irrespective of the thickness of the composite resin.

Example 28

The adhesive strength with respect to both an enamel and a dentin was evaluated in the composition of Example 20 in the case where the thickness of the composite resin was 2.5 mm. Example 28 exhibited low adhesive strength with respect to an enamel and a dentin.

Examples 29 to 32

The measurement was conducted using composite resins in which the contents of the basic inorganic material were different. As a result, compared with Example 28, Examples 29 to 32 exhibited enhanced adhesive strength with respect to an enamel and a dentin in a test chip in which the thickness of the composite resin was 2.5 mm, since the composite resin contained hydroperoxide and the primer contained a vanadium compound. Further, Example 32 using FASG capable of eluting polyvalent metal ions exhibited higher adhesive strength.

Examples 33 to 35

The measurement was conducted using composite resins in which the contents of hydroperoxide were different. As a result, Example 35 containing a larger amount of hydroperoxide exhibited higher adhesive strength compared with Examples 33 and 34.

Examples 36 to 39

The measurement was conducted using composite resins in which the kinds of hydroperoxide and the photopolymerization initiator were different. Even in the case of using any of the hydroperoxides and the photopolymerization initiators, stable adhesive strength was exhibited in the case where the thickness of the composite resin was 2.5 mm. However, Examples 38 and 39 exhibited slightly decreased adhesive strength compared with Examples 36 and 37, since Examples and 39 used CQ and BN that were α-diketone-based photopolymerization initiators.

Examples 40 and 43

Examples 40 and 43 were evaluated varying the content ratio of the filler in the same composition of the radical-polymerizable monomer having no acidic group. As a result, satisfactory adhesive strength was exhibited.

Examples 41 and 42

Examples 41 and 42 were evaluated, in which the photoacid generators of different kinds and CQ that was an α-diketone-based photopolymerization initiator were added in the same composition of the radical-polymerizable monomer having no acidic group as that in Example 40. The α-diketone-based photopolymerization initiator was activated due to the function of the photoacid generator, and hence, the primer and the composite resin were allowed to adhere to each other with satisfactory strength.

Examples 44 and 45

The measurement was conducted using the primers in which the contents of a vanadium compound were different.

As a result, compared with Example 32, Examples 44 and 45 containing a larger amount of the vanadium compound exhibited higher adhesive strength.

Examples 47 and 48

Example 47 in which MF that was a polyvalent metal ion eluting filler was added to a primer and Example 48 in which fumed silica subjected to surface treatment and MF were added as an inorganic filler were evaluated. As a result, in a test chip in which the thickness of the composite resin was 2.5 mm, compared with Example 46, the adhesive strength with respect to an enamel and a dentin was enhanced in both Examples 47 and 48.

Examples 49 and 50

Examples 49 and 50 were evaluated, in which the kind of the organic solvent was varied in the composition of a primer to which a photopolymerization initiator and two kinds of fillers were added. As a result, satisfactory adhesive strength was exhibited.

Next, the results obtained by conducting the similar evaluation regarding the examples (examples 51 to 60) in the first embodiment with respect to the examples (examples 1 to 14, 16 to 50) in the second embodiment will be described.

Examples 51 and 52

Examples 51 and 52 were evaluated using a composite resin containing, as a radical-polymerizable monomer, a radical-polymerizable monomer having no acidic group and containing no tertiary amine compound and no basic inorganic material, and varying the kind of the primer. In Examples 51 and 52, although each adhesive strength was hardly changed for the thickness of 0.5 mm of the composite resin, each adhesive strength was largely decreased for the thickness of 1.5 mm of the composite resin, compared with Examples 3 and 27.

Examples 53 and 54

Examples 53 and 54 were evaluated using a composite resin containing, as a radical-polymerizable monomer, a radical-polymerizable monomer having no acidic group and containing tertiary amine compound and no basic inorganic material, and varying the kind of the primer. In Examples 53 and 54, although each adhesive strength was hardly changed for the thickness of 0.5 mm of the composite resin, each adhesive strength was largely decreased for the thickness of 1.5 mm of the composite resin, compared with Examples 3 and 27.

Example 55

Example 55 was evaluated using a composite resin containing, as a radical-polymerizable monomer, a radical-polymerizable monomer having no acidic group and containing basic inorganic material and no tertiary amine compound, and varying the kind of the primer. In Example 55, although each adhesive strength was hardly changed for the thickness of 0.5 mm of the composite resin, each adhesive strength was largely decreased for the thickness of 1.5 mm of the composite resin, compared with Example 27.

Comparative Example 6

Comparative Example 6 was evaluated, in which a composite resin containing a radical-polymerizable monomer having an acidic group, a tertiary amine compound, and a basic inorganic material was used, and a primer having the same composition as that in Example 27 was blended. As a result, first, the adhesive strength was decreased largely in the case where the thickness of the composite resin was 1.5 mm, compared with the case where the thickness of the composite resin was 0.5 mm. Further, the adhesive strength with respect to a dentin was decreased irrespective of the thickness, compared with that in Example 27.

Examples 57 and 58

Examples 57 and 58 were evaluated using a composite resin containing, as a radical-polymerizable monomer, a radical-polymerizable monomer having no acidic group and containing no tertiary amine compound and no basic inorganic material, and varying the kind of the primer. In Examples 57 and 58, adhesive strength with respect to an enamel and a dentin was decreased for the thickness of 2.5 mm of the composite resin, compared with Examples 32 and 47. In particular, the adhesive strength with respect to a dentin was decreased largely.

Examples 59 and 60

Examples 59 and 60 were evaluated using a composite resin containing, as a radical-polymerizable monomer, a radical-polymerizable monomer having no acidic group and containing hydroperoxide, tertiary amine compound and no basic inorganic material, and varying the kind of the primer. In Examples 59 and 60, adhesive strength with respect to an enamel and a dentin was decreased for the thickness of 2.5 mm of the composite resin, compared with Examples 32 and 47. In particular, the adhesive strength with respect to a dentin was decreased largely.

INDUSTRIAL APPLICABILITY

The present invention can be used in the field of a dental treatment of restoring a loss of a tooth.

The invention claimed is:
1. A dental filling/restoration kit, comprising:
a filling/restoring material (A) containing 100 parts by mass of a radical-polymerizable monomer having no acidic group (a) containing 5 to 25 parts by mass of a water-soluble radical-polymerizable monomer having no acidic group (a1), 0.01 to 5 parts by mass of a photopolymerization initiator (b), and 195 to 2,000 parts by mass of a filler (c), 0.5 to 2 parts by mass of a tertiary amine compound (d), and a basic inorganic material (e); and
a pretreatment material (B) containing a radical-polymerizable monomer having an acidic group (f) and water (g),
wherein the filling/restoring material (A) is directly filled in a cavity coated with the pretreatment material (9), which is uncured.
2. A dental filling/restoration kit according to claim 1, wherein the photopolymerization initiator (b) comprises an acylphosphine oxide-based polymerization initiator.
3. A dental filling/restoration kit according to claim 1, wherein the filling/restoring material (A) comprises at least 3 parts by mass of the basic inorganic material (e) based on 100 parts by mass of the radical-polymerizable monomer having no acidic group (a).

4. A dental filling/restoration kit according to claim 1, wherein the tertiary amine compound (d) is an aromatic amine compound.

5. A dental filling/restoration kit according to claim 1, wherein the basic inorganic material (e) is fluoroaluminosilicate glass.

6. A dental filling/restoration kit according to claim 1, wherein the pretreatment material (B) and the filling/restoring material (A) further comprise a vanadium compound and hydroperoxide, respectively.

* * * * *